United States Patent
Bierman et al.

(10) Patent No.: US 8,211,063 B2
(45) Date of Patent: Jul. 3, 2012

(54) SIDE LOADED SECUREMENT DEVICE

(75) Inventors: Steven F. Bierman, Del Mar, CA (US);
Richard A. Pluth, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 0 days.

(21) Appl. No.: 12/296,262

(22) PCT Filed: Apr. 9, 2007

(86) PCT No.: PCT/US2007/008671
§ 371 (c)(1),
(2), (4) Date: Mar. 4, 2009

(87) PCT Pub. No.: WO2007/117655
PCT Pub. Date: Oct. 18, 2007

(65) Prior Publication Data
US 2009/0254040 A1    Oct. 8, 2009

Related U.S. Application Data

(60) Provisional application No. 60/790,344, filed on Apr. 7, 2006.

(51) Int. Cl.
*A61M 5/32* (2006.01)
(52) U.S. Cl. ........ 604/174; 604/177; 604/178; 604/179; 604/180
(58) Field of Classification Search ................... 604/174, 604/180, 179, 175, 177, 178; 128/207.17, 128/207.18
See application file for complete search history.

(56) References Cited

U.S. PATENT DOCUMENTS

| | | | |
|---|---|---|---|
| 2,525,398 A | 10/1950 | Collins |
| 2,533,961 A | 12/1950 | Rousseau et al. |
| 2,707,953 A | 5/1955 | Ryan |
| 3,059,645 A | 10/1962 | Hasbrouck et al. |
| 3,064,648 A | 11/1962 | Bujan |

(Continued)

FOREIGN PATENT DOCUMENTS
EP        0064284 A2    11/1982
(Continued)

OTHER PUBLICATIONS

International Search Report and Written Opinion, PCT Application No. PCT/US007/08671, mailed May 8, 2008, 9 pages.

*Primary Examiner* — Kevin C Sirmons
*Assistant Examiner* — Bradley Thomas, Jr.
(74) *Attorney, Agent, or Firm* — Knobbe Martens Olson & Bear, LLP

(57) ABSTRACT

An anchoring system includes a device which permits a portion of a catheter or similar medical article to be easily anchored to a patient, desirably without the use of tape or needles and suture. The anchoring system comprises an anchor pad and a retainer mounted upon the anchor pad. The retainer includes at least one clip forming at least a portion of a central channel and that moves generally in a lateral direction to capture the medical article to be retained. In certain embodiments, the clip moves in lateral and transverse directions between closed and open positions. The medical article is secured within the central channel. The channel may have a straight or tapering shape depending on the medical article to be retained.

22 Claims, 21 Drawing Sheets

U.S. PATENT DOCUMENTS

| | | | |
|---|---|---|---|
| 3,482,569 A | 12/1969 | Raffaelli | |
| 3,602,227 A | 8/1971 | Andrew | |
| 3,613,663 A | 10/1971 | Johnson | |
| 3,630,195 A | 12/1971 | Santomieri | |
| 3,677,250 A | 7/1972 | Thomas | |
| 3,766,915 A | 10/1973 | Rychlik | |
| 3,834,380 A | 9/1974 | Boyd | |
| 3,856,020 A | 12/1974 | Kovac | |
| 3,863,527 A | 2/1975 | Berning | |
| 3,906,946 A | 9/1975 | Nordström | |
| 3,973,565 A | 8/1976 | Steer | |
| 4,020,835 A | 5/1977 | Nordstrom et al. | |
| 4,057,066 A | 11/1977 | Taylor | |
| 4,059,105 A | 11/1977 | Cutruzzula et al. | |
| 4,129,128 A | 12/1978 | McFarlane | |
| 4,142,527 A | 3/1979 | Garcia | |
| 4,161,177 A | 7/1979 | Fuchs | |
| 4,165,748 A | 8/1979 | Johnson | |
| 4,193,174 A | 3/1980 | Stephens | |
| 4,224,937 A | 9/1980 | Gordon | |
| 4,248,229 A | 2/1981 | Miller | |
| 4,250,880 A | 2/1981 | Gordon | |
| 4,275,721 A | 6/1981 | Olson | |
| 4,284,076 A | 8/1981 | Hall | |
| 4,316,461 A | 2/1982 | Marais et al. | |
| 4,326,519 A | 4/1982 | D'Alo et al. | |
| 4,333,468 A | 6/1982 | Geist | |
| 4,362,156 A | 12/1982 | Felle et al. | |
| 4,392,853 A | 7/1983 | Muto | |
| 4,397,647 A | 8/1983 | Gordon | |
| 4,405,312 A | 9/1983 | Gross et al. | |
| 4,449,975 A | 5/1984 | Perry | |
| 4,453,933 A | 6/1984 | Speaker | |
| 4,480,639 A | 11/1984 | Peterson et al. | |
| 4,627,842 A | 12/1986 | Katz | |
| 4,683,882 A | 8/1987 | Laird | |
| 4,711,636 A | 12/1987 | Bierman | |
| 4,737,143 A | 4/1988 | Russell | |
| 4,742,824 A | 5/1988 | Payton et al. | |
| 4,792,163 A | 12/1988 | Kulle | |
| 4,808,162 A | 2/1989 | Oliver | |
| 4,822,342 A | 4/1989 | Brawner | |
| 4,832,019 A | 5/1989 | Weinstein et al. | |
| 4,846,807 A | 7/1989 | Safadago | |
| 4,852,844 A | 8/1989 | Villaveces | |
| 4,857,058 A | 8/1989 | Payton | |
| 4,863,432 A | 9/1989 | Kvalo | |
| 4,897,082 A | 1/1990 | Erskine | |
| 4,898,587 A | 2/1990 | Mera | |
| 4,919,654 A | 4/1990 | Kalt | |
| 4,921,199 A | 5/1990 | Villaveces | |
| 4,932,943 A | 6/1990 | Nowak | |
| 4,955,864 A | 9/1990 | Hajduch | |
| 4,976,700 A | 12/1990 | Tollini | |
| 4,986,815 A | 1/1991 | Schneider | |
| 5,037,397 A | 8/1991 | Kalt et al. | |
| 5,069,206 A | 12/1991 | Crosbie | |
| 5,073,170 A | 12/1991 | Schneider | |
| 5,084,026 A | 1/1992 | Shapiro | |
| 5,098,399 A | 3/1992 | Tollini | |
| 5,147,322 A | 9/1992 | Bowen et al. | |
| 5,156,641 A | 10/1992 | White | |
| 5,192,273 A | 3/1993 | Bierman et al. | |
| 5,192,274 A | 3/1993 | Bierman | |
| 5,195,981 A | 3/1993 | Johnson | |
| 5,236,421 A | 8/1993 | Becher | |
| 5,266,401 A | 11/1993 | Tollini | |
| 5,267,967 A | 12/1993 | Schneider | |
| 5,290,248 A | 3/1994 | Bierman et al. | |
| 5,292,312 A | 3/1994 | Delk et al. | |
| 5,304,146 A | 4/1994 | Johnson et al. | |
| 5,306,243 A | 4/1994 | Bonaldo | |
| 5,314,411 A | 5/1994 | Bierman et al. | |
| 5,322,097 A | 6/1994 | Wright | |
| 5,338,308 A | 8/1994 | Wilk | |
| 5,342,317 A | 8/1994 | Claywell | |
| 5,344,406 A | 9/1994 | Spooner | |
| 5,352,211 A | 10/1994 | Merskelly | |
| 5,354,282 A | 10/1994 | Bierman | |
| 5,372,589 A | 12/1994 | Davis | |
| 5,380,293 A | 1/1995 | Grant | |
| 5,380,395 A | 1/1995 | Uchida | |
| 5,382,239 A | 1/1995 | Orr et al. | |
| 5,402,776 A | 4/1995 | Islava | |
| 5,403,285 A | 4/1995 | Roberts | |
| 5,413,562 A | 5/1995 | Swauger | |
| 5,443,460 A | 8/1995 | Miklusek | |
| 5,456,671 A | 10/1995 | Bierman | |
| 5,468,231 A | 11/1995 | Newman et al. | |
| 5,470,321 A | 11/1995 | Forster et al. | |
| D364,922 S | 12/1995 | Bierman | |
| 5,496,282 A | 3/1996 | Militzer et al. | |
| 5,496,283 A | 3/1996 | Alexander | |
| 5,499,976 A | 3/1996 | Dalton | |
| 5,520,656 A | 5/1996 | Byrd | |
| 5,527,293 A | 6/1996 | Zamierowski | |
| 5,531,695 A | 7/1996 | Swisher | |
| 5,549,567 A | 8/1996 | Wolman | |
| D375,355 S | 11/1996 | Bierman | |
| 5,578,013 A | 11/1996 | Bierman | |
| 5,593,395 A | 1/1997 | Martz | |
| 5,637,098 A | 6/1997 | Bierman | |
| 5,685,859 A | 11/1997 | Kornerup | |
| 5,693,032 A | 12/1997 | Bierman | |
| 5,722,959 A | 3/1998 | Bierman | |
| 5,755,225 A | 5/1998 | Hutson | |
| 5,810,781 A | 9/1998 | Bierman | |
| 5,833,666 A * | 11/1998 | Davis et al. | 604/180 |
| 5,911,707 A | 6/1999 | Wolvek et al. | |
| 6,067,985 A | 5/2000 | Islava | |
| 6,132,399 A | 10/2000 | Shultz | |
| 6,213,979 B1 | 4/2001 | Bierman | |
| 6,228,064 B1 | 5/2001 | Abita et al. | |
| 6,283,945 B1 | 9/2001 | Bierman | |
| 6,287,281 B1 | 9/2001 | Nishtala et al. | |
| 6,428,515 B1 | 8/2002 | Bierman et al. | |
| 6,488,664 B1 | 12/2002 | Solomon et al. | |
| 6,491,664 B2 | 12/2002 | Bierman | |
| 6,582,403 B1 | 6/2003 | Bierman et al. | |
| 7,413,561 B2 | 8/2008 | Raulerson et al. | |
| 7,776,017 B2 | 8/2010 | Ponzi et al. | |
| 7,799,001 B2 | 9/2010 | Bierman | |
| 2001/0011164 A1 * | 8/2001 | Bierman | 604/180 |
| 2002/0165493 A1 * | 11/2002 | Bierman | 604/174 |
| 2007/0173766 A1 | 7/2007 | Bierman | |
| 2009/0299294 A1 | 12/2009 | Pinkus | |

FOREIGN PATENT DOCUMENTS

| | | |
|---|---|---|
| EP | 356683 A1 | 3/1990 |
| FR | 2381529 | 2/1978 |
| GB | 2086466 | 5/1982 |
| GB | 2211417 | 7/1989 |
| WO | WO 80/01458 | 7/1980 |
| WO | WO 92/19309 | 11/1992 |
| WO | WO 94/12231 | 6/1994 |
| WO | WO 97/15342 | 5/1997 |
| WO | WO 2005/105194 A1 | 11/2005 |
| WO | WO 2008/151047 A1 | 12/2008 |

\* cited by examiner

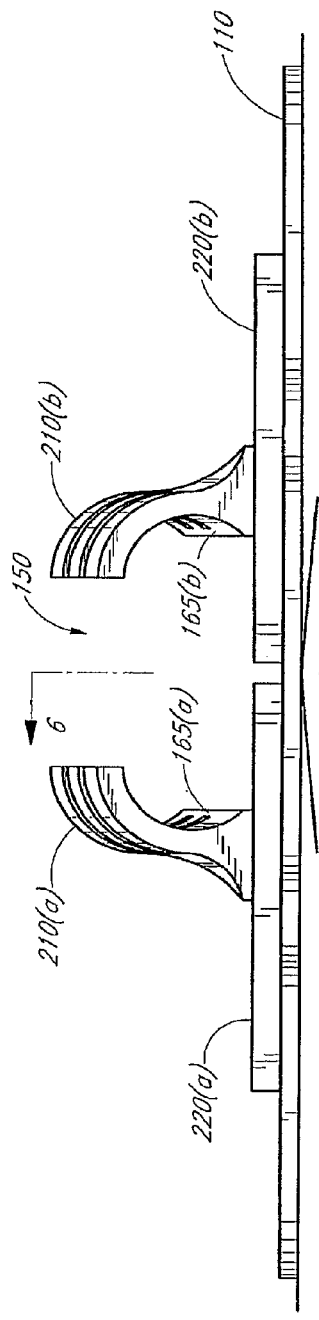
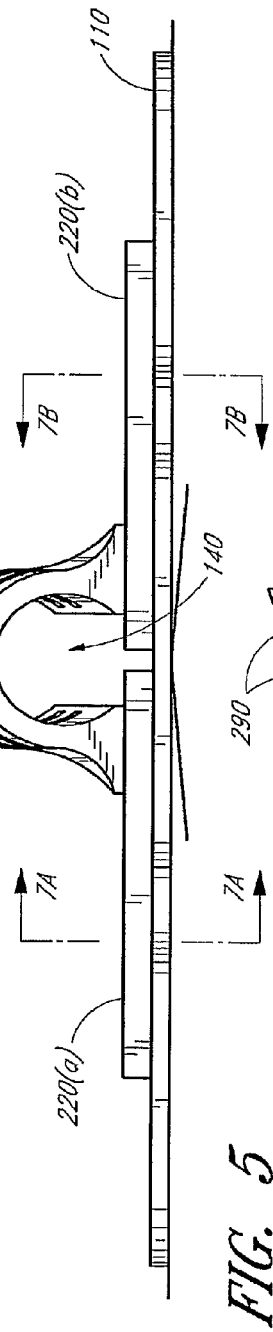
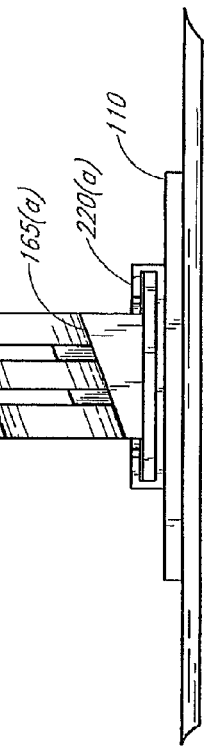
FIG. 4
FIG. 5
FIG. 6

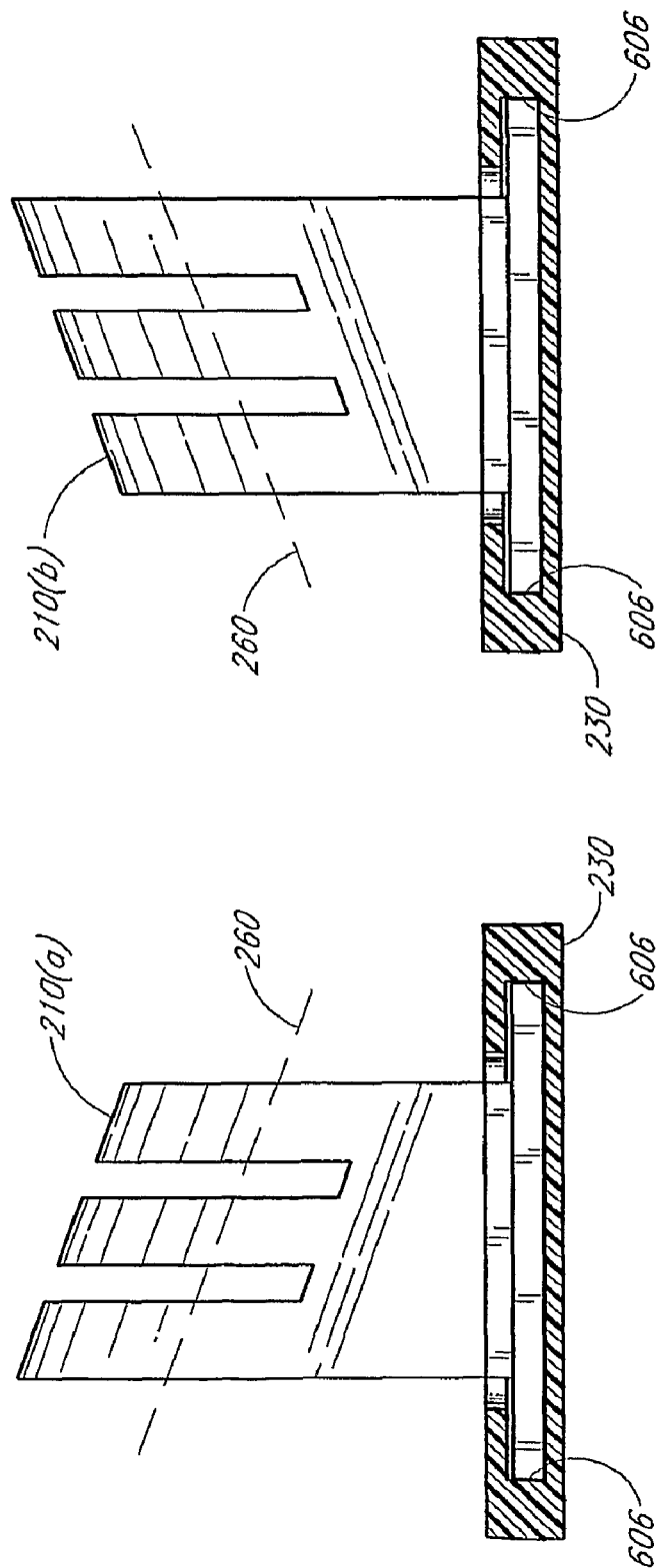

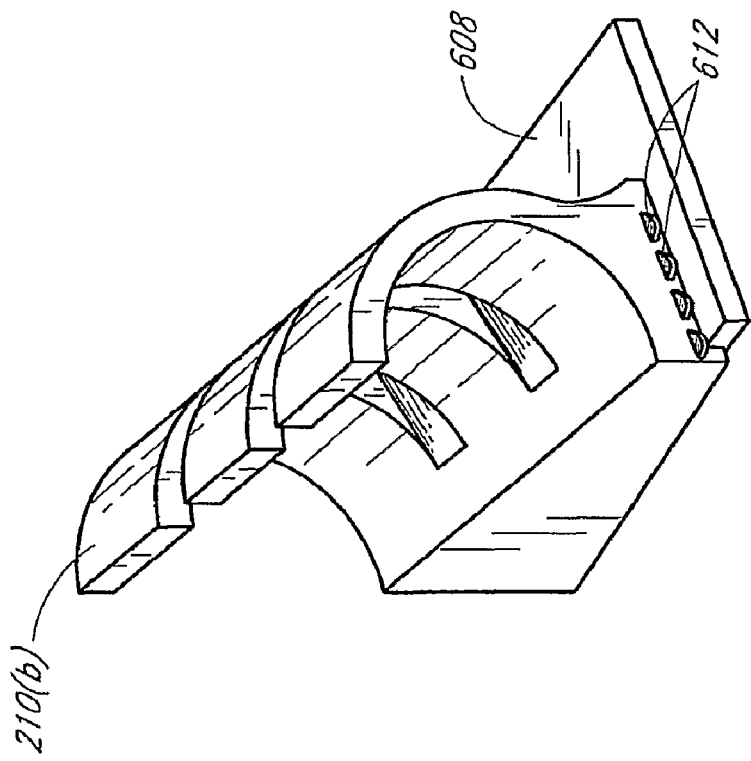
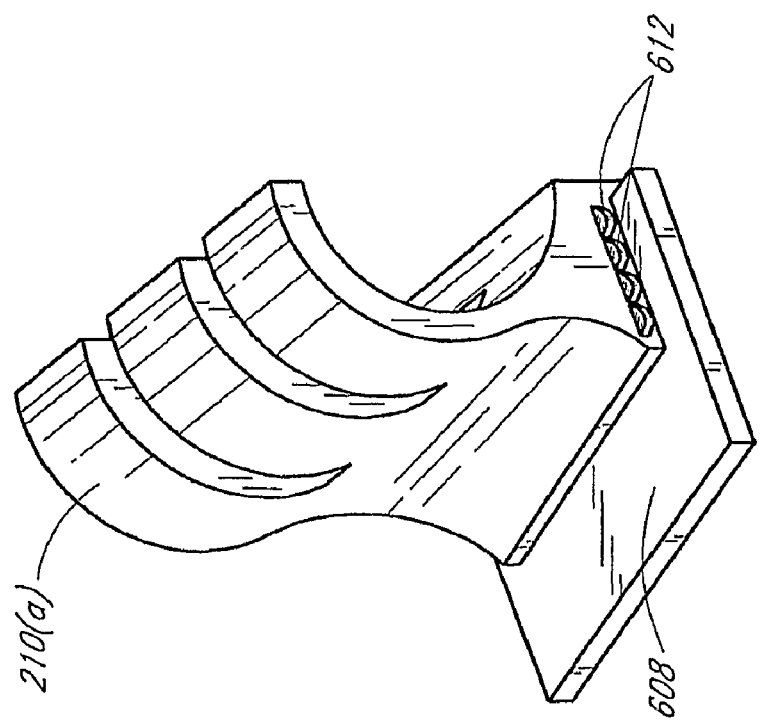
FIG. 8B
FIG. 8A

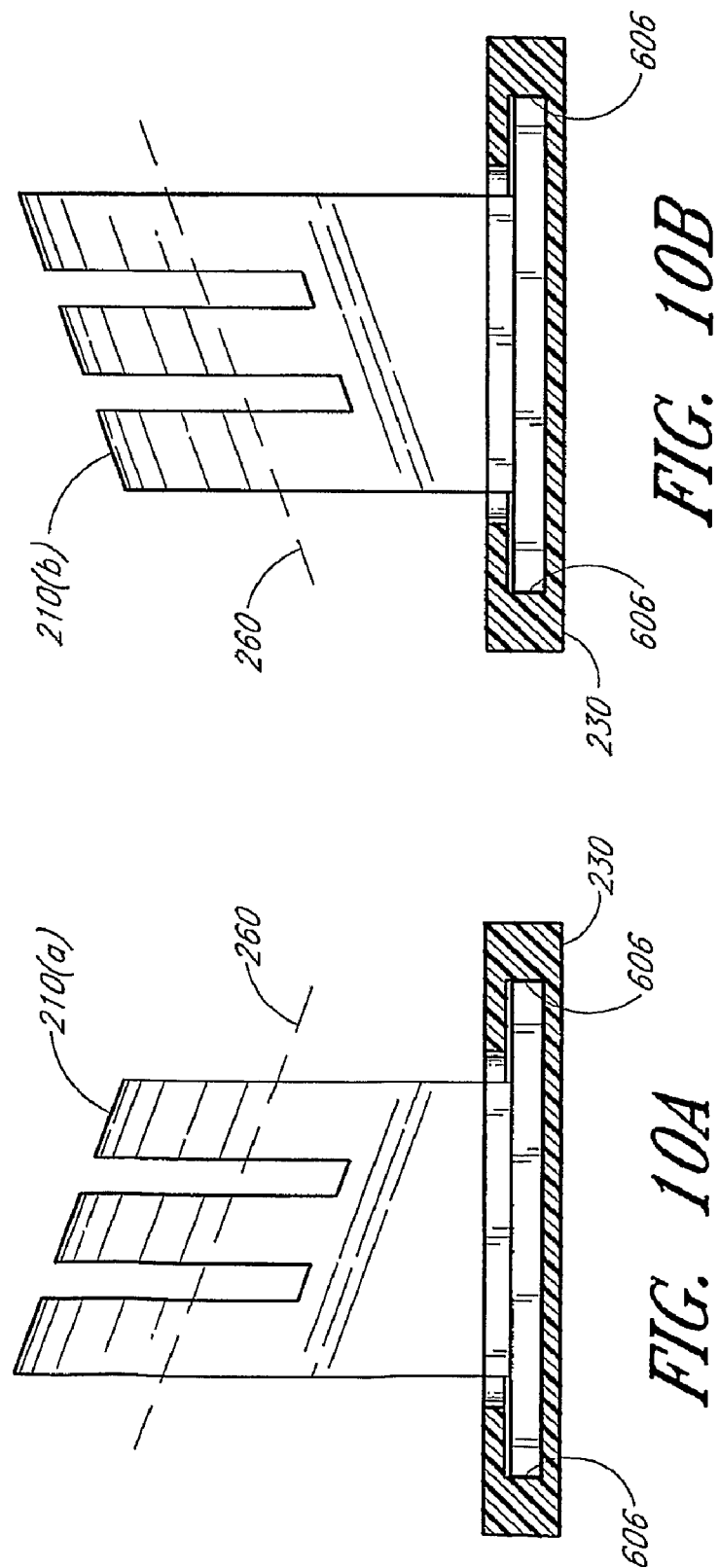

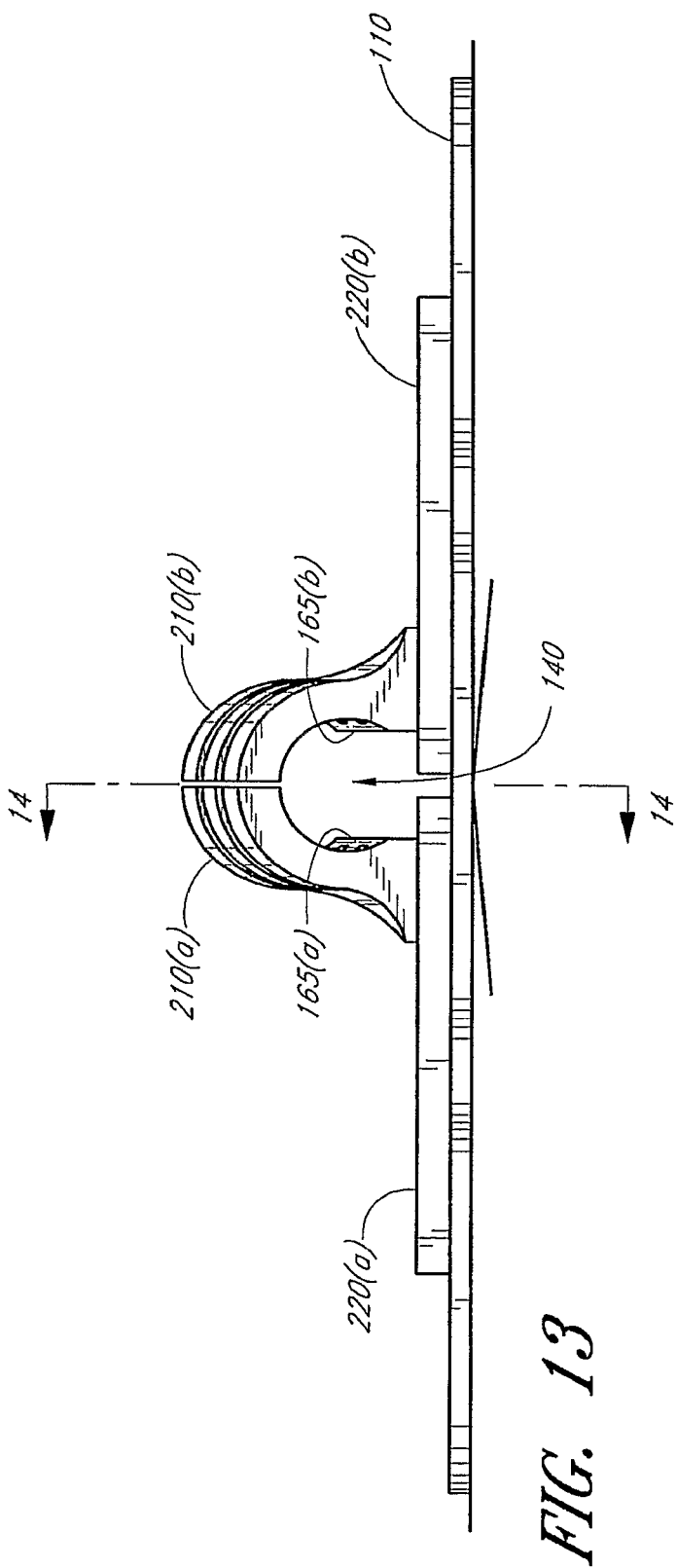
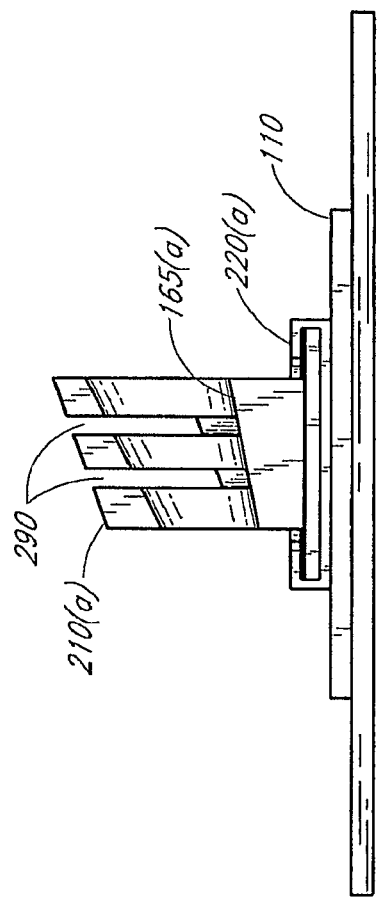
FIG. 13
FIG. 14

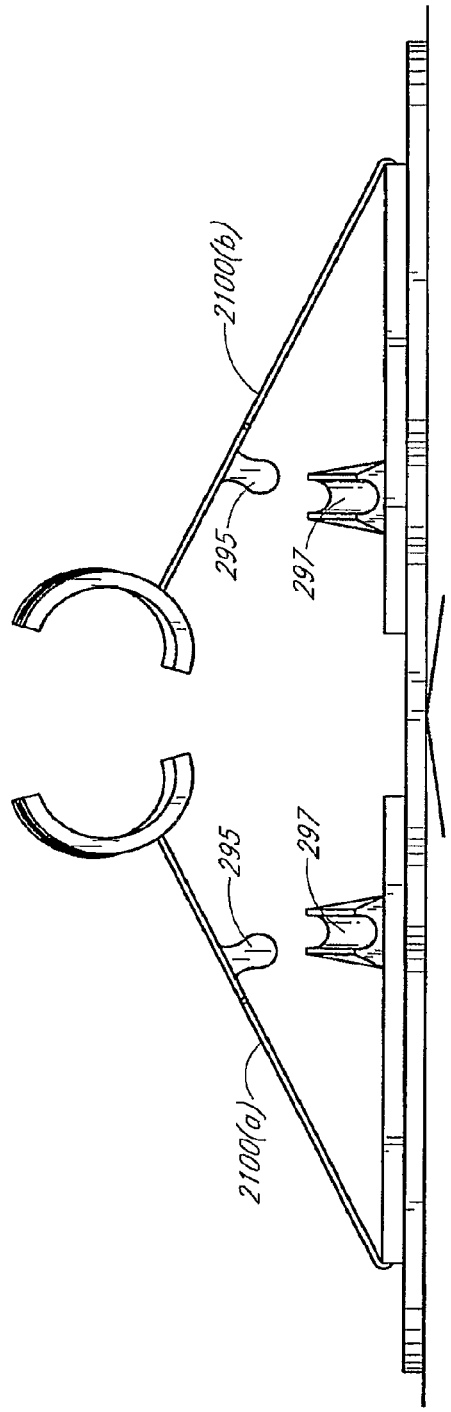
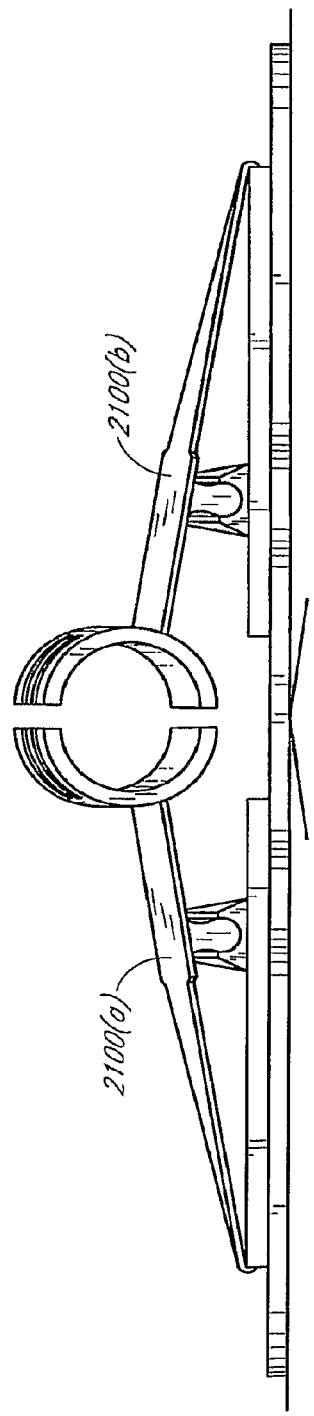

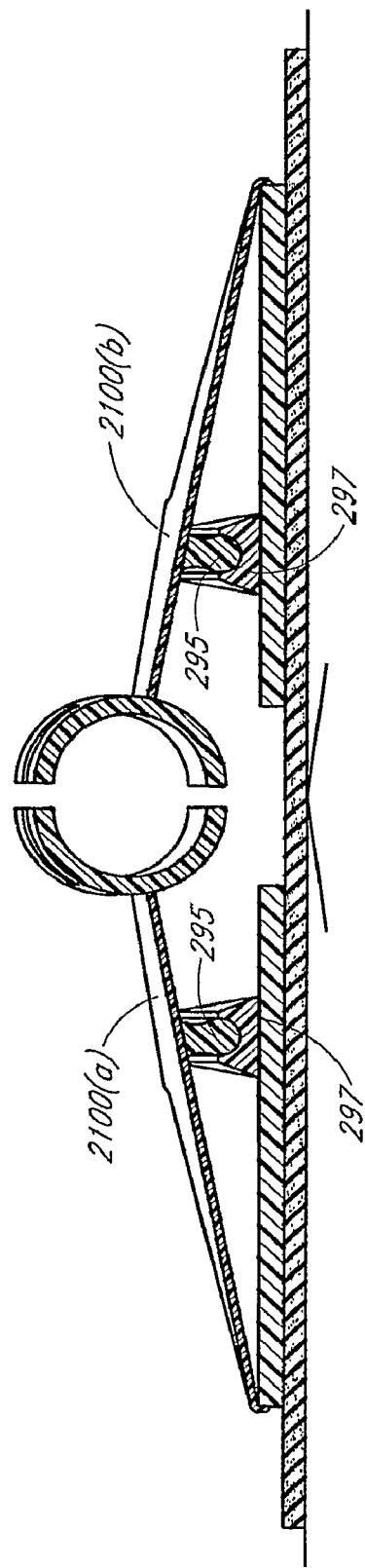

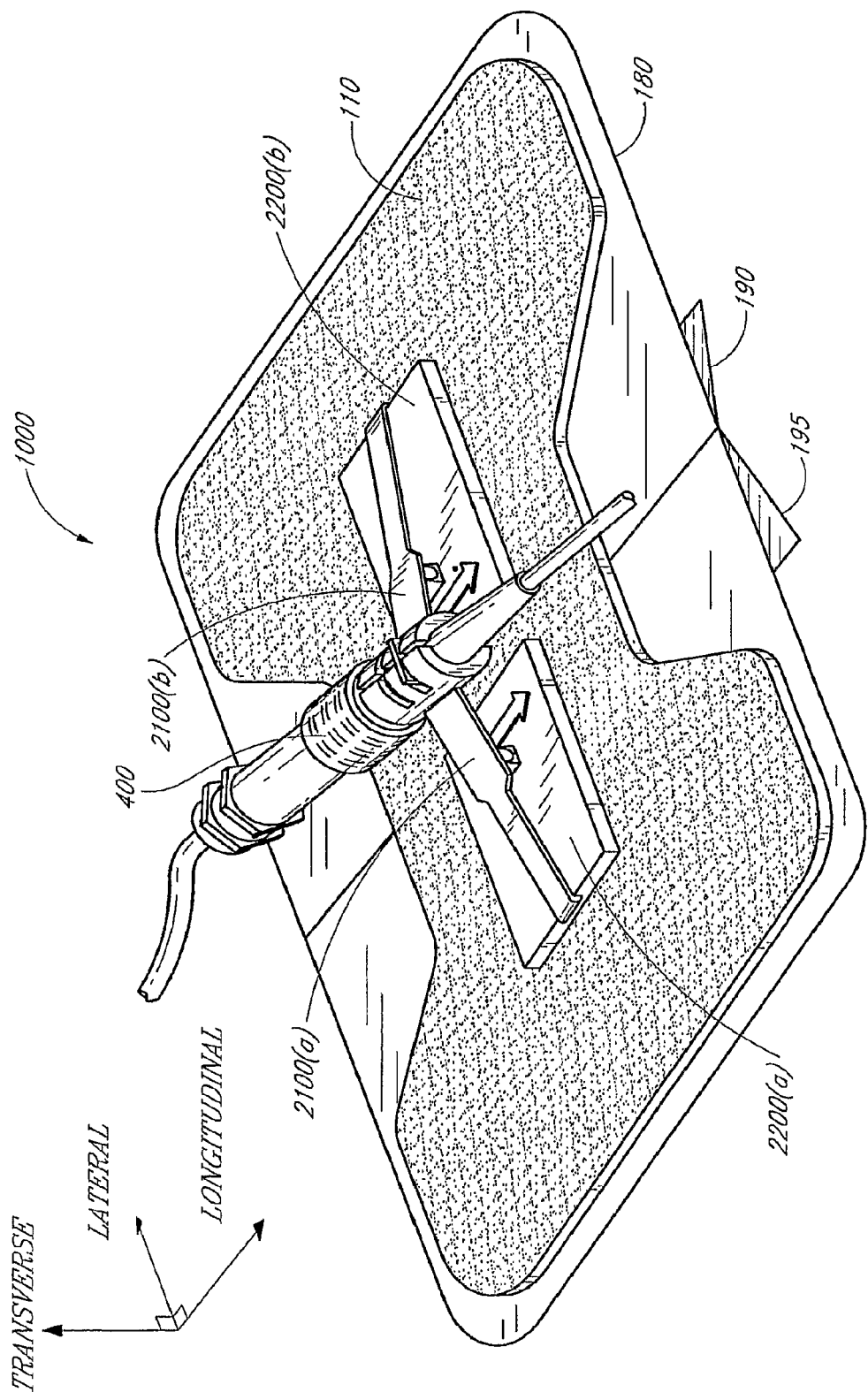

US 8,211,063 B2

SIDE LOADED SECUREMENT DEVICE

RELATED APPLICATIONS

This application claims the benefit of U.S. Provisional Patent No. 60/790,344, filed Apr. 7, 2006, which is hereby incorporated by reference in its entirety.

BACKGROUND OF THE INVENTION

1. Field of the Invention

This invention relates to a securement system used to attach a medical article to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line can be secured to the patient in a variety of ways. Most commonly, this involves taping the catheter or medical line to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue can also make the catheter or medical line stickier and more difficult to handle for healthcare providers.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional catheter securement systems.

An aspect of the invention is a securement system comprising a retainer, an anchor, and a medical article. The retainer comprises two clips which are movable in at least a lateral direction with respect to one another to establish a closed condition and an open condition. The clips cooperate to form a channel when the retainer is in the closed condition. The first clip has at least one surface extending in a direction normal to the axis of the channel of the retainer. The anchor supports the retainer so that the clips are inhibited from moving generally in the direction normal to the axis of the channel. The medical article has an elongated body and at least one radially extending member that extends from the elongated body in a direction normal to the axis of the elongated body. The radially extending member abuts the at least one surface of the retainer when the retainer is in the closed condition to inhibit longitudinal motion of the medical article through the retainer.

Another aspect of the invention is a securement device for securing a medical article having an elongated body to a body of a patient. The securement device comprises a flexible anchor and a retainer attached to an upper side of the anchor. The flexible anchor has a mounting surface which is at least partially covered by an adhesive layer for attaching the securement device to the patient's body. The retainer has two clips, each clip having a groove. At least one of the clips is movable in at least a transverse direction so as to define a channel between the clips when in a closed position, the channel being formed by the grooves in the clips.

A further aspect of the invention is a securement system comprising a retainer and a medical article. The retainer comprises a body having two portions which are movable in a lateral direction with respect to one another to establish a closed condition and an open condition. The two portions cooperate to form a channel when the retainer is in the closed condition. One portion of the body has at least one surface extending in a direction normal to the axis of the channel of the retainer. The medical article has an elongated body and at least one member that extends radially from the elongated body in a direction normal to the axis of the elongated body. The radially extending member of the medical article abuts the at least one surface of the retainer when the retainer is in the closed condition to inhibit longitudinal motion of the medical article through the retainer.

A still further aspect of the invention is a method of releasably securing a medical article to a retainer. The method includes the step of providing a medical article and a retainer, where the medical article has an elongated body and at least one radially extending member extending from the body in a direction normal to the axis of the body. The retainer has two clips and two bases. Each clip slidingly engages one of the bases, and each clip has a groove. In their closed configuration, the clips are slid toward each other and moved relative to the bases. In their open configuration, the clips are slid away from each other and moved relative to the bases. When the retainer is in the closed position, the grooves of the clips cooperate to form a channel. The retainer further includes at least one slot disposed along the length of the channel. The method further includes the steps of sliding the clips in opposite directions along an axis to place the retainer in the open configuration, placing the elongated body of the medical article between the first and second grooves of the retainer, and coarsely aligning the radially extending member with the slot. The method also includes the step of attaching the medical article to the retainer by sliding the clips in opposite directions along the axis to place the retainer in the closed configuration and capture the radially extending member in the slot.

BRIEF DESCRIPTION OF THE DRAWINGS

FIG. 4 is a front side view of the retainer of FIG. 2 in an open position.

FIG. 5 is a front side view of the retainer of FIG. 2 in a closed position.

FIG. 6 is a cross-section view of the retainer taken along section 6-6 of FIG. 4.

FIG. 7A is a left side view of the retainer taken along section 7A-7A of FIG. 5.

FIG. 7B is a right side view of the retainer taken along section 7B-7B of FIG. 5.

FIG. 8A is a perspective view of a left movable clip of the retainer from FIG. 2.

FIG. 8B is a perspective view of a right movable clip of the retainer from FIG. 2.

FIG. 10A is a left side view of the retainer taken along section 10A-10A of FIG. 9.

FIG. 10B is a right side view of the retainer taken along section 10B-10B of FIG. 9.

FIG. 13 is a front side view of the retainer from FIG. 9 in a closed position.

FIG. 14 is a cross-section view of the retainer taken along section 14-14 of FIG. 13 and showing the tapering inner channel.

FIG. 18 is a front side view of the securement device from FIG. 16 with the retainer shown in an elevated and open position.

FIG. 19 is a front side view of the securement device from FIG. 16 in a lowered and closed position.

FIG. 20 is a cross-section of the retainer taken along section 20-20 of FIG. 17.

FIG. 21 is a perspective view of a securement device including a retainer having a tapered inner channel and movable clips comprising lever arms, configured in accordance with another preferred embodiment of the present invention and shown securing an exemplary medical article.

DETAILED DESCRIPTION OF THE PREFERRED EMBODIMENTS

The following description and the accompanying figures, which describe and show the preferred embodiments, are made to demonstrate several possible configurations that a securement system can take to include various aspects and features the invention. To facilitate a complete understanding of the embodiments, the remainder of the detailed description describes the securement system with reference to the figures, wherein like elements among the embodiments are referenced with like numerals throughout the following description.

A "longitudinal axis" is generally parallel to a portion of the connector fitting or other medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein. Also, the terms "proximal" and "distal", which are used to describe the present securement system, are used consistently with the description of the exemplary applications (i.e., the illustrative example of the use application). Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. The term "radially extending member" as user herein refers to a structure that extends in an outward direction from a medical article such that the radially extending member has at least a lateral and/or a transverse component. Accordingly, a radially extending member need not extend entirely in the lateral and/or transverse directions and may instead extend in any direction away from the longitudinal axis.

Figure 1:
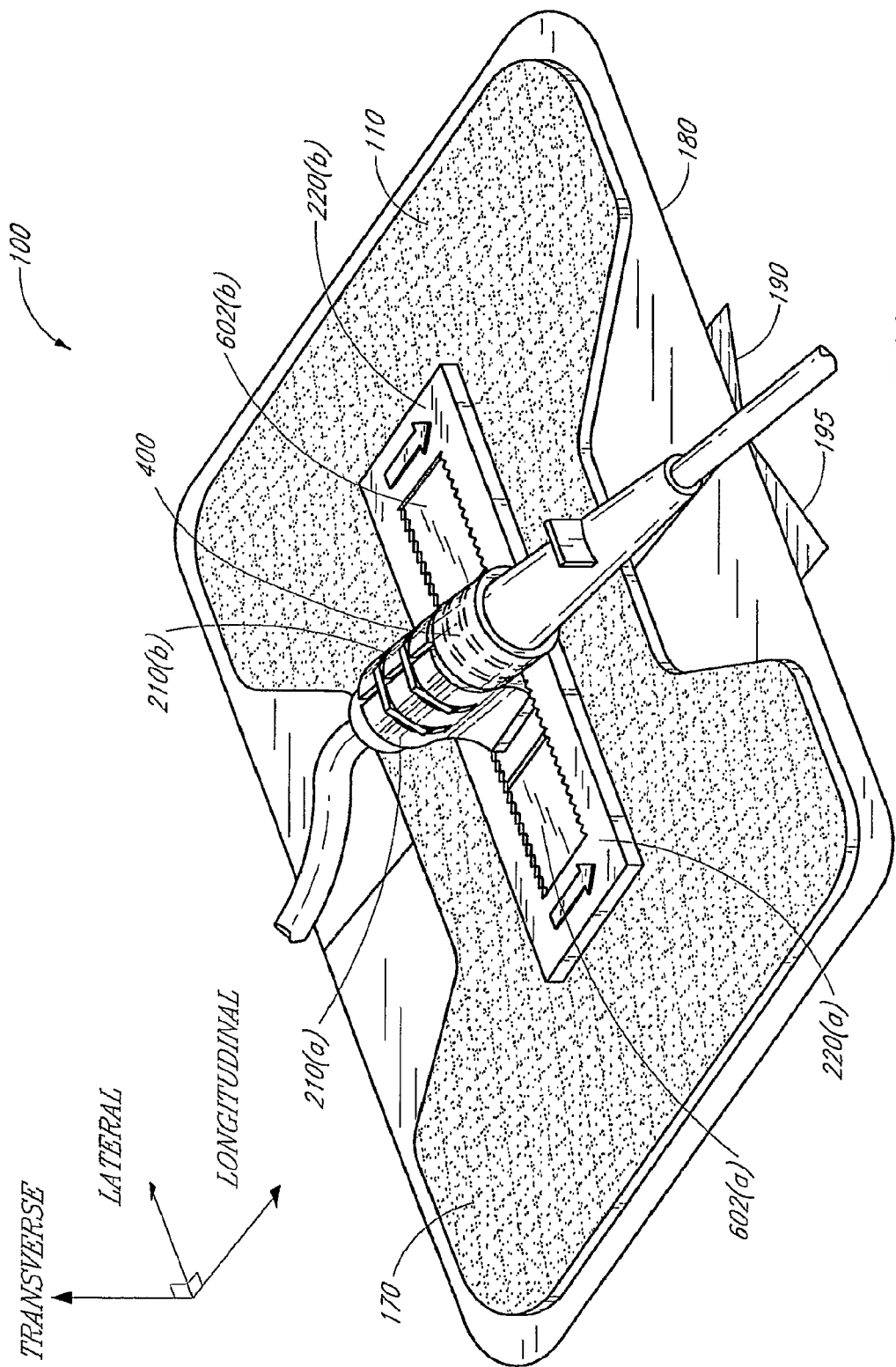
FIG. 1 is a perspective view of a securement device configured in accordance with a preferred embodiment of the present invention and shown securing an exemplary medical article.
Figure 2:
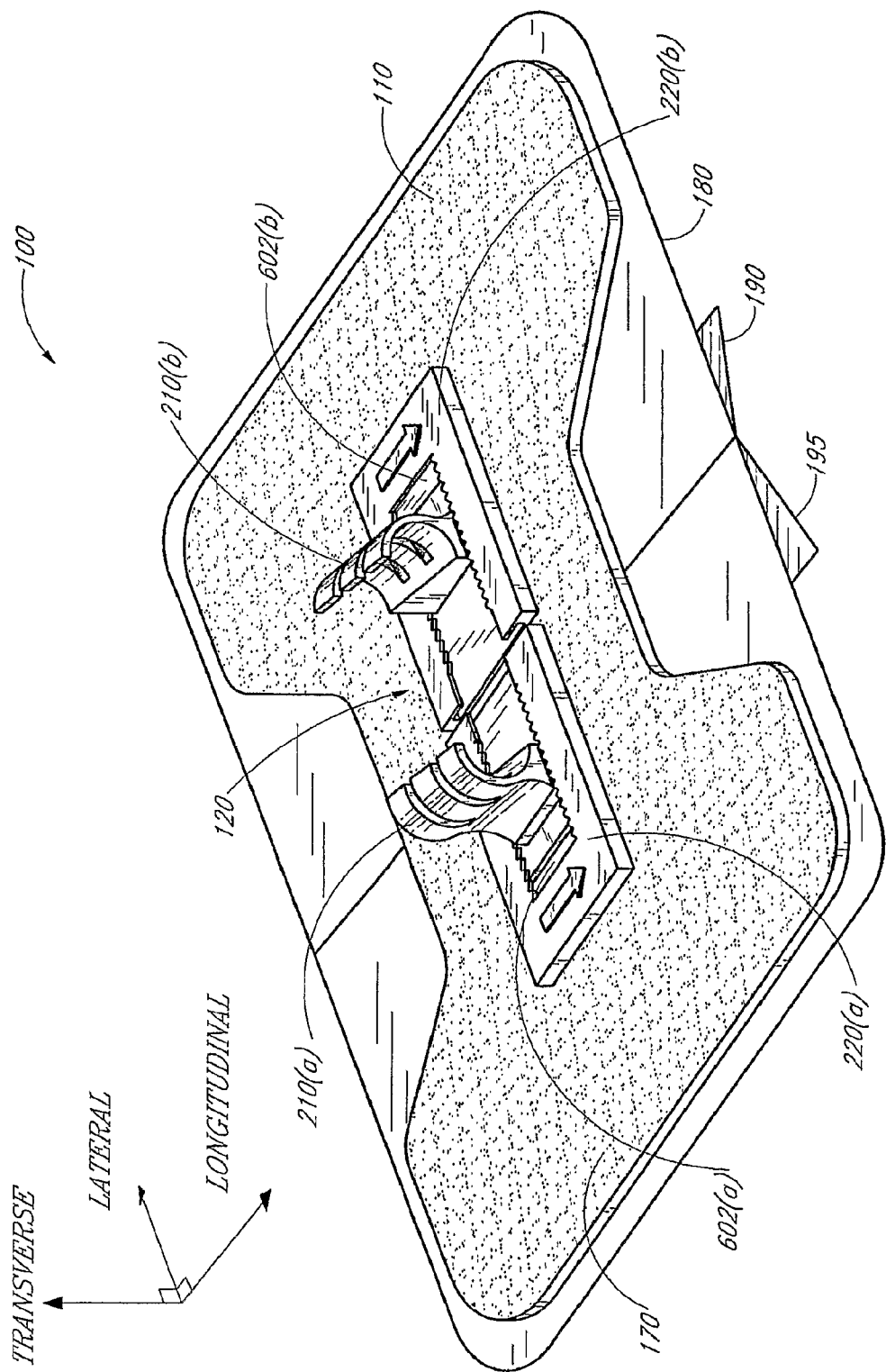
FIG. 2 is perspective view of the securement device from FIG. 1 shown in an open position.
Figure 3:
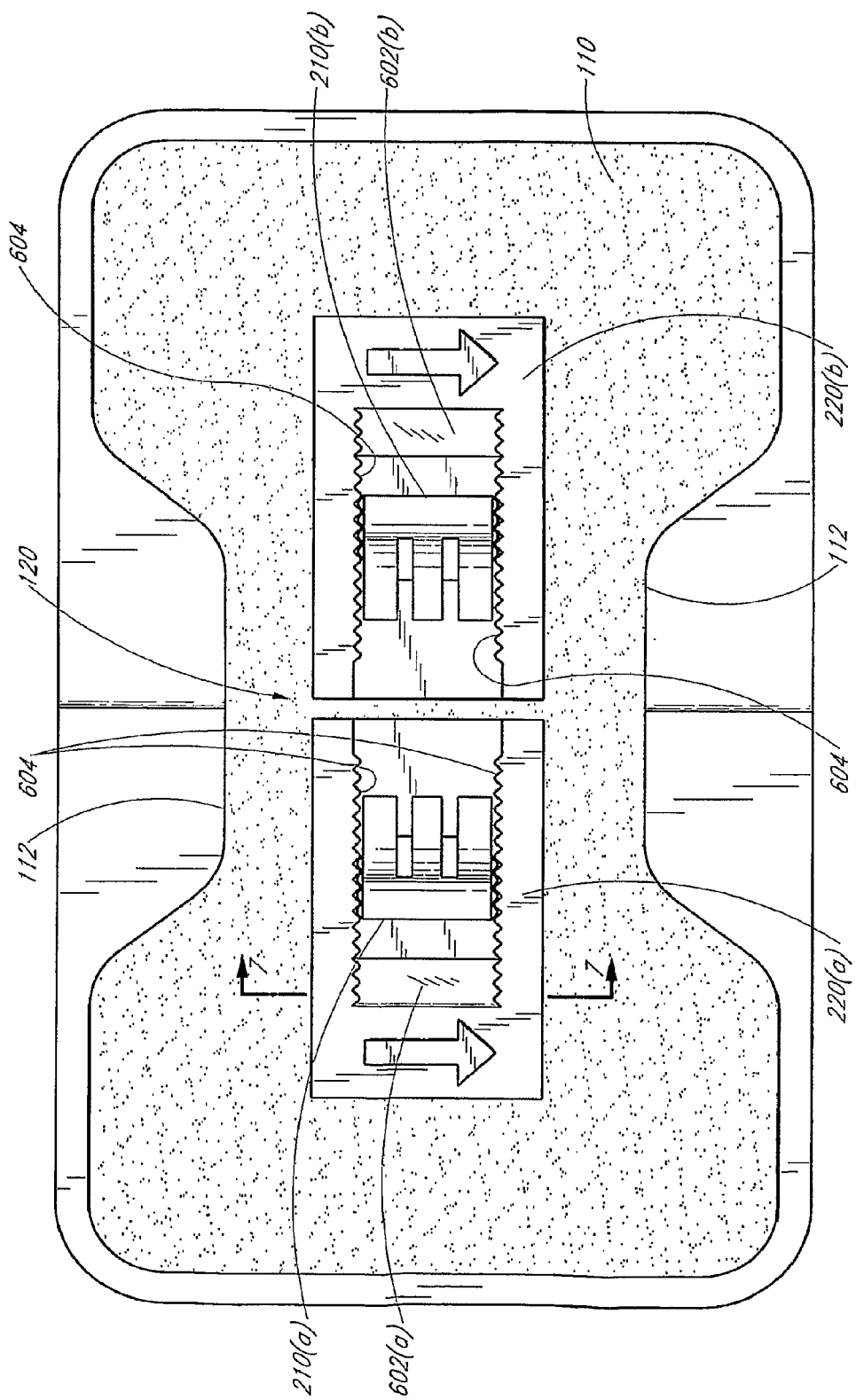
FIG. 3 is a top plan view of the securement device of FIG. 2 which includes a retainer having movable clips and a ratchet arrangement.

FIGS. 1 and 2 show perspective views of a securement device 100 configured in accordance with a preferred embodiment of the present invention. FIG. 1 illustrates the device 100 in a closed position, securing an exemplary medical article 400. FIG. 2 shows the securement device 100 in an open position. FIG. 3 is a top plan view of same device 100. As shown in FIGS. 1 through 3, the illustrated securement device 100 comprises two main components: an anchor pad 110 and a retainer 120. The illustrated retainer 120 includes a left movable clip 210(*a*), a right movable clip 210(*b*), and a pair of corresponding bases 220(*a*), 220(*b*). The terms "clips" is used herein as a general term for two structures that together form a securement region or channel. Although only a single shape of the clip is illustrated in FIGS. 1 through 3, those of skill in the art will recognize that a variety of shapes can be used. In the embodiment illustrated in FIG. 2, each movable clip 210 slidingly engages one of the bases 220. The bases 220(*a*), 220(*b*) are disposed upon the anchor pad 110. The left and right movable clips 210(*a*), 210(*b*) generally move in a lateral direction away from and toward a center of the retainer 120.

In the preferred embodiment illustrated in FIGS. 1 through 3, both clips 210(*a*), 210(*b*) are movable. However, only one of the two clips 210 need move to allow ingress and egress into the securement device 100. For example, the clip 210(*a*) may be fixed to the anchor pad 110 or base 220(*a*) with the clip 210(*b*) being movable. In this way, movement of a single clip 210(*b*) places the securement device 100 in the open and closed positions.

When moving between the open and closed positions, the clips 210(*a*), 210(*b*) are illustrated moving in a lateral direction so as to capture the medical article 400 therebetween. However, the clips need not move only in the lateral direction between the open and closed positions. For example, the clips may move in transverse and lateral directions as is illustrated by the embodiment in FIG. 16. Preferably, movement of at least one of the clips 210 between the open and closed positions includes a lateral component and side loads the medical article 400.

Although illustrated securing an exemplary medical article 400, the securement device 100 can form a component of a catheterization or securement system that includes one or more of various medical articles, such as connector fittings, catheters, hubs, catheter adaptors, fluid supply lines, or other articles suitable for securement via the anchor pad and retainer. The anchor or anchor pad 110 is secured to the skin of the patient, generally by an adhesive disposed upon the bottom surface of the anchor. The medical article is then disposed between the open movable clips, aligned with the channel, and secured within the channel by closing the movable clips. In this way, the retainer 120 secures the medical article to the patient. Thus, the retainer 120 at least restricts, if not prevents, lateral and transverse movement of the retained section of the medical article. Additional features of the securement device 100 can restrict, if not prevent, longitudinal movement of the retained section of the medical article. The embodiments of the anchor and the retainer are described in more detail below.

Anchor Pad

The general structure of the anchor pad 110 comprises a generally rectangular shape with scalloped regions 112 (see FIG. 3) located near the middle of the anchor pad 110. The scalloped configuration eases the process of aligning the securement device with a catheter insertion site in the patient's skin. Although only a single shape of the anchor pad is illustrated in FIGS. 1 through 3, those of skill in the art will recognize that a variety of shapes can be used.

The anchor pad 110 desirably comprises a laminate structure with an upper plastic, paper or foam layer (e.g., closed-cell polyethylene foam) and a lower adhesive layer. The lower adhesive layer constitutes a lower surface of the anchor pad. The lower surface desirably is a medical-grade adhesive and can be either diaphoretic or nondiaphoretic, depending upon the particular application. Such foam with an adhesive layer is available commercially from Avery Dennison of Painesville, Ohio. While not illustrated, the anchor pad 110 can include suture holes in addition to the adhesive layer to further secure the anchor pad to the patient's skin.

In other variations, a hydrocolloid adhesive or zinc oxide-based adhesive can advantageously be used upon the anchor pad 110 for attaching the anchor pad to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, the anchor pad 110 comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface of the anchor pad. The lower surface desirably is a medical-grade adhesive and can be either diaphoretic or nondiaphoretic, depending upon the particular application.

A surface of the upper foam layer constitutes an upper surface 170 of the anchor pad 110. The upper surface 170 can be roughened by corona-treating the foam with a low electric charge. The roughened or porous upper surface can improve the quality of the adhesive joint (which is described below) between the bases 220(*a*), 220(*b*) and the anchor pad 110. In a further variation, the flexible anchor pad can comprise an upper paper or other woven or nonwoven cloth or plastic layer in lieu of a roughened upper foam surface.

As illustrated in FIG. 1, a removable paper or plastic release liner 180 desirably covers the adhesive lower surface before use. The liner 180 preferably resists tearing and desirably is divided into a plurality of pieces to ease attachment of the pad 110 to a patient's skin.

The liner 180 comprises a folded over portion to define a pull tab 190. The pull tab can be utilized to remove the paper or plastic release liner 180 from the adhesive lower surface before use. A healthcare provider uses the pull tab 190 by grasping and pulling on it so that the liner 180 is separated from the lower surface. The pull tab 190 overcomes any requirement that the healthcare provider pick at a corner edge or other segment of the liner in order to separate the liner from the adhesive layer.

The pull tab 190 of course can be designed in a variety of configurations. For example, the pull tab 190 can be located along a center line of the anchor pad 110; or alternatively, the pull tab can be located along any line of the anchor pad 110 in order to ease the application of the anchor pad onto the patient's skin at a specific site. For example, an area of a patient's skin with an abrupt bend, such as at a joint, can require that the pull tab 190 be aligned toward one of the lateral ends of the anchor pad 110 rather than along the center line. In the embodiment illustrated in FIGS. 1 through 3, the pull tab 190 extends from a bottom surface of the anchor pad 110 and along an outer line 195.

Retainer

An embodiment of the retainer 120 is described with reference to FIGS. 2 through 8. FIG. 4 is a front side view of the retainer 120 of FIG. 2 in an open position. FIG. 5 is a front side view of the retainer 120 of FIG. 2 in a closed position. FIG. 6 is a cross-section view of the retainer 120 taken along section 6-6 of FIG. 4.

FIG. 2 illustrates the clips 210(*a*), 210(*b*) and corresponding ratchets 602(*a*), 602(*b*) configured to receive and retain the clips 210 in multiple positions. The clips 2109*a*), 210(*b*) may be placed in one of these positions and allows the retainer 120 to accommodate medical articles 400 with different lateral or transverse widths. The general structure of the clips 210(*a*), 210(*b*) and bases 220(*a*), 220(*b*) are separate members that slidably engage each other. Of course the bases 220(*a*), 220(*b*) may have a unitary structure and still allow at least one clip 210 to move in the lateral direction. Further, the clip and base could have a unitary structure that still allows the clip to move relative to the base.

The clips 210 are slidably mounted on the respective bases 220 and together secure the medical article 400 to the retainer 120. Each clip 210 includes a first interengagement structure which cooperates with a second interengagement structure on the base 220. In the illustrated embodiment, the first engagement structure includes a tongue structure and the second engagement structure includes a corresponding groove. The groove includes a ratchet 602 element which permits motion of the clip 210 relative to the base 220 in one or both directions. For example, the ratchet 602 may be configured to only allow the clip 210 to move from an open position to a closed position. The embodiment illustrated in FIG. 2 allows the clip 210 to move in both directions relative to the base 220. Because the clips 210 slide from the sides toward the longitudinal axis, the retainer 120 captures the medical article therebetween. The retainer 120 accommodates variations in the widths of the medical article.

The ratchet element 602 extends generally in a lateral direction. The base 220 and the ratchet element 602 are preferably formed as one piece. Although only a single arrangement of the ratchet element 602 and the base 220 is illustrated in FIGS. 1 through 3, those of skill in the art will recognize that a variety of arrangements can be used. For example, the base 220 and ratchet element 602 could be formed in layers. The clip 210 is slidably mounted in this channel-like ratchet element 602.

The movable clips 210(a), 210(b) are elongated in the longitudinal direction and when in a closed position comprise a generally parallelepiped shape. It is advantageous for the longitudinal dimension of the movable clips 210(a), 210(b) to be sufficiently long to provide stability to the retained portion of the medical article 400 along its length. In this way, the longitudinal length of the retained portion is sufficient to inhibit rocking of the medical article 400 within the retainer 120. Also, the lateral dimension of the movable clips 210(a), 210(b) of the retainer desirably allows the healthcare provider to easily and naturally grip the retainer 120.

With reference to FIG. 5, the inner sides of the movable clips 210(a) 210(b) face towards each other and preferably define a central channel 140 in the closed position. The channel 140 extends between the movable clips 210(a), 210(b) in a longitudinal direction for receiving a section of the medical article 400.

The channel 140 is capable of receiving a portion or length of the medical article 400 and is generally configured to house, to preferably grip, and to secure this portion of the medical article. In the illustrated embodiment, the central channel 140 has a generally semi-circular cross-sectional shape when the retainer 120 is in the closed position (see FIG. 5). An inner surface contour of the central channel 140 preferably is selected depending on the geometry of the portion of the medical article to be retained. For example, in a retainer 120 that is configured to retain a portion of a medical article 400 that has a constant outer diameter, the central channel 140 preferably has a constant radius along its length. By matching the inner surface contour of the central channel 140 to the outer surface of the secured portion of the medical article, a more effective securement may be achieved.

The movable clips 210(a), 210(b) of the retainer 120 illustrated in FIG. 2 preferably are configured to retain a portion of a medical article that has a generally constant outer radius along its length. The inner surface of the central channel 140 is sized to match or approximately match the outer radius of the medical article. To arrest longitudinal motion of the medical article, one or more abutment surfaces on the movable clips 210(a), 210(b) contact one or more contact surfaces on the medical article 400. Each abutment surface can cooperate with a contact surface on the medical article to inhibit movement of the medical article relative to the retainer 120. Exemplary abutment surfaces include the surfaces at the longitudinal ends of the movable clips 210(a), 210(b) and the inner surfaces of the slots 290 in the movable clips 210(a), 210(b) (see FIG. 6). Exemplary contact surfaces include a radially extending member of the medical article 400 such as members 370 or tabs 310 (see FIGS. 1 and 25).

The inner surface of the central channel 140 may be selected to match the outer surface of the medical article 400 when the movable clips 210(a), 210(b) are in a completely closed position or a partially closed position. Other embodiments of the retainer 120 can have an inner surface that is configured to match, or closely match, an outer surface of a raised portion of a connector fitting 300 portion of the medical article 400 (see, e.g., FIG. 25).

Although the central channel 140 can be formed in various shapes depending upon the desired application (e.g., depending upon a shape of the retained portion of the medical article for which the retainer is designed to be used), the central channel 140 desirably has a sufficient length in the longitudinal direction to stabilize the connector fitting, catheter hub, or other medical article, rather than act as a fulcrum for the fitting, as mentioned above. That is, the retainer 120 receives a sufficient length of the catheter hub to inhibit movement of the hub in the lateral, longitudinal and transverse direction (i.e., to inhibit yaw, pitch and axial movement of the article).

FIGS. 7A and 7B show left and right side views of the retainer 120 from FIG. 2. FIGS. 8A and 8B show perspective views of the left and right movable clips 210(a) and 210(b), respectively. The clips 210 and the bases 220 each include at least one row of interengaging ratchet teeth 604 (FIG. 3) aligned with interengaging pawls 612 (FIGS. 8A and 8B). The teeth 604 and the pawls 612 may be disposed on a side edge between each clip 210 and the respective base 220. The interengaging structure maintains the clips 210 in a manually selected position.

The ratchet teeth 604 are formed on the inner sides or lateral, flat surfaces of the ratchet elements 602 and are aligned in a lateral direction with each tooth extending radially towards the lateral axis. In a preferred form of the invention, the ratchet teeth 604 are formed in only a portion of each of the side walls of the channel-like ratchet elements 602.

The interengaging pawls 612 are resiliently formed into a portion of the sides of the clips 210 and are aligned so as to be parallel to the side walls of the channel-like ratchet elements 602. The interengaging pawls 612 cooperate with the teeth of the ratchet elements 602 to manually fix the position of each clip 210 or sides of the central channel 140.

The clips 210 and the bases 220 include an interengaging tongue 608 portion and a corresponding groove(s) 606, respectively. In a preferred form, the grooves 606 are formed in portions of the side walls of the channel-like ratchet element 602 that are located below the teeth 604 and above a bottom surface of the channel-like ratchet element 602. The tongue 608 is formed along a lower portion of the clip 210 and extends parallel to the pawls 612. At least a portion of the tongue 608 extends in a longitudinal direction beyond at least a portion of the jagged outer periphery of the pawl 612. The tongue 608 and grooves 606 cooperate to guide the pawls 612 between the facing rows of teeth 604 and further limit longitudinal movement of the clip 210 relative to the base 220 when the sides of the tongue 608 are seated within the grooves 606. Thus, the combination of the engagement between the teeth 604 and the pawl 612 along with the engagement between the tongue 608 and the grooves 606 inhibits transverse and longitudinal movements of the clip 210 relative to the base 220 while permitting some lateral movement between the open and closed positions.

Alternatively, the location of the pawls 612, the teeth 604, the tongue 608 and the grooves 606 are reversed. In such an arrangement, the pawls 612 and teeth 604 are located below the tongue 608 and grooves 606.

Alternatively, both rows of teeth 604 are slightly rotated towards each other and about axes which are parallel to the lateral axis to form a channel-like ratchet element 602 with side walls that converge in a radial direction away from the lateral axis. The sides of the pawl 612 are angled towards each other so as to align with the teeth 604 when the clip 210 is inserted into the ratchet element 602. By angling the walls of the teeth 604 and pawls 612, the engagement between the teeth 604 and the pawl 612 inhibits transverse, lateral, and longitudinal movements of the clip 210 relative to the base 220 without a tongue 608 and groove 606 arrangement.

Because conventional medical articles have dimensional variations, it is desirable that the clip 210 be adjustable to accommodate the various sizes and yet securely hold the medical article relative to the retainer 120. The clips 210 are movable laterally along the ratchet elements 602, and the ratchet teeth 604 cooperate with the clip pawls 612 to resist lateral movement and hold the clip 210 in the manually selected position.

As shown most clearly in FIG. 4, the upper side of the retainer 120 includes an access or opening 150 formed when the movable clips 210(a), 210(b) are slid in a lateral direction away from each other. The movable clips 210(a), 210(b) need not be slid the same distance in the lateral direction. One movable clip 210(a) may be slid further in the lateral direction than the other movable clip. Further, the movable clips 210(a), 210(b) may be slid different amounts for different medical articles depending on the lateral width of the medical article to be retained. Of course, only one of the movable clips 210(a), 210(b) need be slid to access or close the channel 140. The other movable clip 210(a) may be stationary when the retainer is moved between the open and closed positions. Thus, some embodiments have a fixed clip 210(a) and a movable clip 210(b). The medical article 400 may be inserted into the channel 140 through the opening 150 but also may be inserted into the channel along the longitudinal axis.

The illustrated retainer 120 further comprises at least one retention surface 165(a), 165(b) disposed on a lower side of the channel 140. The retention surface holds at least a portion of the retained medical article within the channel 140 and hence away from the patient's skin when the retainer 120 is in the closed position. This support can be provided by, for example, an adhesive, a region of the channel 140 which provides a degree of snap-fit with the retained medical article 400, or a combination of the adhesive and a region of snap-fit. The adhesive can be located on one or more surfaces of the retainer 120 that contact the medical article. For example, the adhesive could be located on the surface of the channel 140 or on an abutment surface.

As shown most clearly in FIGS. 4 and 6, the illustrated embodiment of the retainer 120 includes multiple pairs of retention surfaces 165(a), 165(b) separated by the slots 290. The corresponding retention surfaces 165(a), 165(b) of each pair lie on opposite sides of the lower region from each other. In this embodiment, the retention surface 165(a) is a portion of the surface that defines the central channel 140 and is located on the lower side of the central channel 140. The retention surface 165(a) is located to one side of the central axis. The other retention surface 165(b) is a portion of the surface that defines the central channel 140 and is located on the lower side of the central channel 140. Once the medical article 400 is placed in the central channel 140 and the clips 210(a), 210(b) moved in a generally sideways direction to the closed position, the retention surfaces 165(a), 165(b) each hold a portion of the retained section of the article 400 within the channel 140. Pressure can be provided by the clips 210(a), 210(b) when in the closed position which holds the medical article 400 within the retainer 120 in the illustrated embodiment.

As shown most clearly in FIG. 5, in one embodiment the arc extends for more than 180 degrees in order to more firmly support the retained portion of the medical article 400. In the illustrated embodiment, the walls of the central channel 140 extend through an arc of approximately 270°. The length of such an arc provides additional contact between the central channel 140 and the secured portion of the medical article. In this way, the secured medical article 400 is less likely to shift within the channel 140.

The retainer 120 can include a generally rigid structure (at least in comparison to foam or tape) and is principally defined by the clips 210(a), 210(b) and bases 220(a), 220(b). The clips 210(a), 210(b) and bases 220(a), 220(b) may be made from materials including, for example, but without limitation; plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials can be utilized.

The bases 220(a), 220(b) of the retainer 120 are attached to the upper surface 170 of the anchor pad 110. The bases 220(a), 220(b) are desirably secured to the upper surface of the pad by a solvent bond adhesive, such as cyanoacrylate or other bonding material. One such adhesive is available commercially as Part No. 4693 from 3M.

When the anchor pad 110 is secured to the skin of the patient, the medical article is inhibited from moving substantially in either the lateral or transverse directions relative to the patient. Longitudinal movement of the medical article 400 is inhibited by engagement between at least one abutment surface on the retainer 120 and a contact surface or mating surface on the medical article 400, such as one or more surfaces of the radially extending members 370 or of the tab 310 (see FIG. 25), or by adhesive. The abutment surface on the retainer 120 preferably extends generally normal to the axis of the central channel 140. The abutment surface can be located at or between the distal and proximal ends of the retainer 120. For example, the abutment surface can be either the proximal or distal ends of the retainer (as will be apparent from the embodiments described later). Moreover, multiple abutment surfaces on the retainer 120 can be employed with each abutment surface being the same or a different type of abutment surface.

The retainer 120 thus preferably includes one or more abutment surfaces. In the illustrated embodiment, the retainer includes multiple abutment surfaces that are formed by one or more slots 290 in the movable clips 210(a), 210(b). In the form of a slot 290, one abutment surface is formed on one side of the slot and another abutment surface is formed on the other side of the same slot 290.

The embodiment illustrated in FIGS. 1 through 8 includes a central channel 140 that has a generally constant cross-sectional shape (e.g., a generally constant diameter to cooperate with a tubular connector fitting body). Thus, to arrest longitudinal motion in the illustrated embodiment, two contact surfaces in the form of a single radially extending member are employed on the medical article. The radially extending member extends through the slot 290 in the retainer 120 to inhibit longitudinal motion of the medical article in both directions. The contact between the two abutment surfaces on the retainer and their corresponding contact surfaces on the medical article 400 arrests motion in the longitudinal direction.

As shown in FIG. 6, the retainer 120 includes pairs of abutment surfaces with each pair forming one lateral slot 290 (preferably four abutment surfaces form at least two slots) that are sized to receive a radially extending portion of the medical article 400 (e.g., a push tab 310 that extends from a catheter hub). These slots 290 can extend circumferentially about at least a portion of the axis of the central channel 140. Preferably, a slot 290 in clip 210(*a*) is aligned in a lateral direction with a slot 290 in clip 210(*b*). Each slot has a longitudinal length sufficient to accept the radially extending member of the retained medical article. Of course only one clip 210 need have a slot 290 to receive a radially extending portion or member such as push tab 310.

The radially extending portion of the medical article 400 is preferably in the form of a push tab 310. In particular, it can be desirable for the longitudinal length of each slot 290 to be sufficient to receive the push tab 310 of the medical article 400; however, each slot 290 can be slightly larger than the push tab's thickness (as measured in the longitudinal direction) and a gap can exist between one or both sides of the push tab 310 and the corresponding abutment surfaces that define the slot 290 into which the push tab 310 has been inserted. In a preferred form, at least two or three annular slots 290 are disposed within the retainer 120. The longitudinal length of each slot 290 preferably is about five thousandths of an inch (0.005 inch, 0.127 mm) larger than the radially extending member (e.g., the push tab 310). Such an arrangement can be desirable to minimize longitudinal movement of the retained portion of the medical article 400. Accordingly, a small gap can exist between any abutment surface and a corresponding contact surface before the medical article 400 is shifted relative to the retainer 120. Once shifted, however, further longitudinal movement is prevented by the interference between the contact surface and the abutment surface.

Those of skill in the art will recognize that each slot 290 need not have identical radial extent. The radial extent of each slot 290 need not be uniform about the axis of the central channel 140 or between the clips 210(*a*), 210(*b*).

The inner edges of each slot 290 can be chamfered so as to ease the insertion of a radially extending member into any slot 290. By having the edges of each slot chamfered, it becomes possible to move a radially extending member into a slot 290 even if the initial alignment between the center of the slot and the center of the radially extending member is not exact. The use of chamfered edges on the slots 290, as well as the presence of slots located at multiple longitudinal positions along the length of the central channel 140, allows for a medical article 400 to be placed into the central channel of the retainer 120 with only coarse alignment with the axis of the central channel. The medical article 400 generally moves into the nearest slot 290 as the movable clips 210(*a*), 210(*b*) are moved to the closed position.

Though not illustrated in FIGS. 7A and 7B, a base surface 230 of the retainer 120 can have a concave curved shape when viewed from the front and rear sides. The degree of curvature can be varied depending on the expected location of usage or application of the securement device 100. It will be appreciated that many common sites for insertion of medical lines which require securement will be located on anatomical regions exhibiting convex curvature, such as a dorsal side of a hand, an arm, a leg, a contact surface, etc. By providing a concave bottom profile to the retainer 120, the retainer will rock less once placed upon the patient via the anchor pad 110.

As is illustrated in FIGS. 7A and 7B, an axis 260 of the central channel 140 lies at an angle with respect to the base surfaces 230 of the retainer 120. The desired angle between the medical article 400 and the patient is created by angling the axis 260 of the central channel 140. This angle is selected in order to align the axis 260 of the channel 140 of the retainer with the desired incident angle with which the medical article is to contact the skin of the patient. A variety of different angles can be used, ranging from 0° to 45°, and more preferably from 5° to 25°. For instance, for the securement of intravenous catheters, it is desirable for the angle of incidence of the catheter to the skin of the patient to be between about 7° to about 15°. For the securement of arterial catheters, it is desirable for the angle of incident of the catheter to the skin of the patient to be about 12.5°. By angling the axis 260 of the channel 140 at the desired angle, which will depend upon the particular securement application (e.g., securing an arterial catheter, an intravenous catheter, etc.), the proper angle of incidence for a catheter can be maintained.

With reference now to FIGS. 9 through 14, a securement device 100 having a tapered inner channel 140 is illustrated. The retainer 120 illustrated in FIGS. 9 through 14 is similar to the retainer 120 illustrated in FIGS. 1 through 8 except that the channel 140 is tapered in the embodiment illustrated in FIGS. 9 through 14 and accommodates a medical article having a tapering outer shape.

Figure 9:
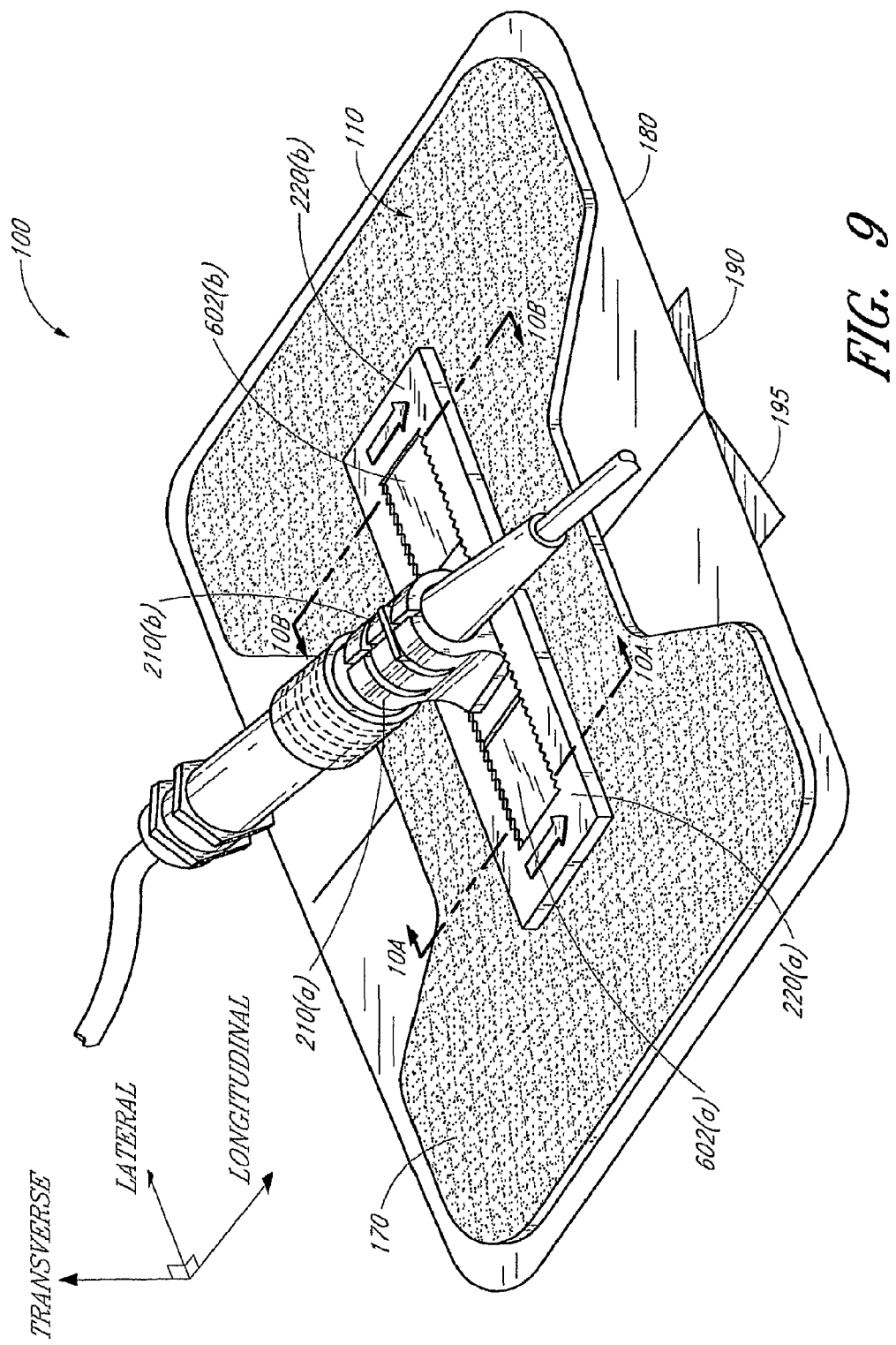
FIG. 9 is a perspective view of a securement device having a tapered inner channel, configured in accordance with another preferred embodiment of the present invention and shown securing an exemplary medical article.
Figure 11B:
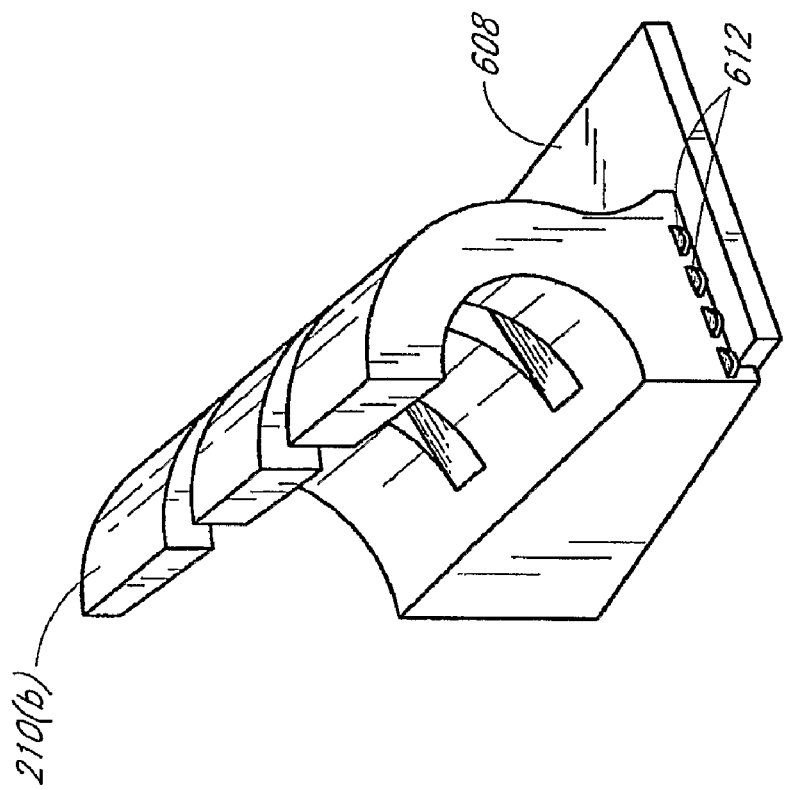
FIG. 11B is a perspective view of a right movable clip from FIG. 9 and having a tapering inner channel.
Figure 11A:
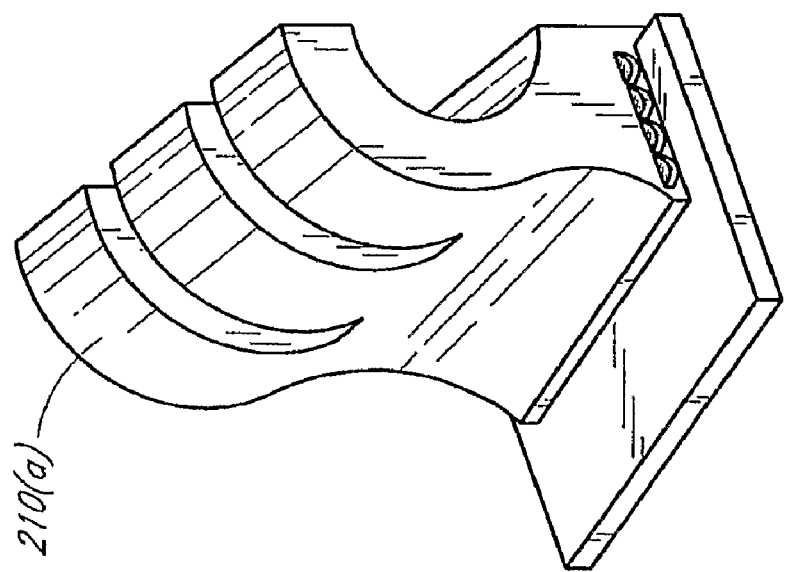
FIG. 11A is a perspective view of a left movable clip from FIG. 9 and having a tapering inner channel.

FIG. 9 is a perspective view of the securement device 100, shown securing the exemplary medical article 400 having a tapering outer shape portion. FIGS. 10A and 10B show left and right side views, respectively, of the retainer 120. The tapered inner channel 140 is best seen in FIGS. 11A and 11B, which show perspective views of left and right movable clips 210(*a*) and 210(*b*), respectively, of the retainer from FIG. 9.

Figure 12:
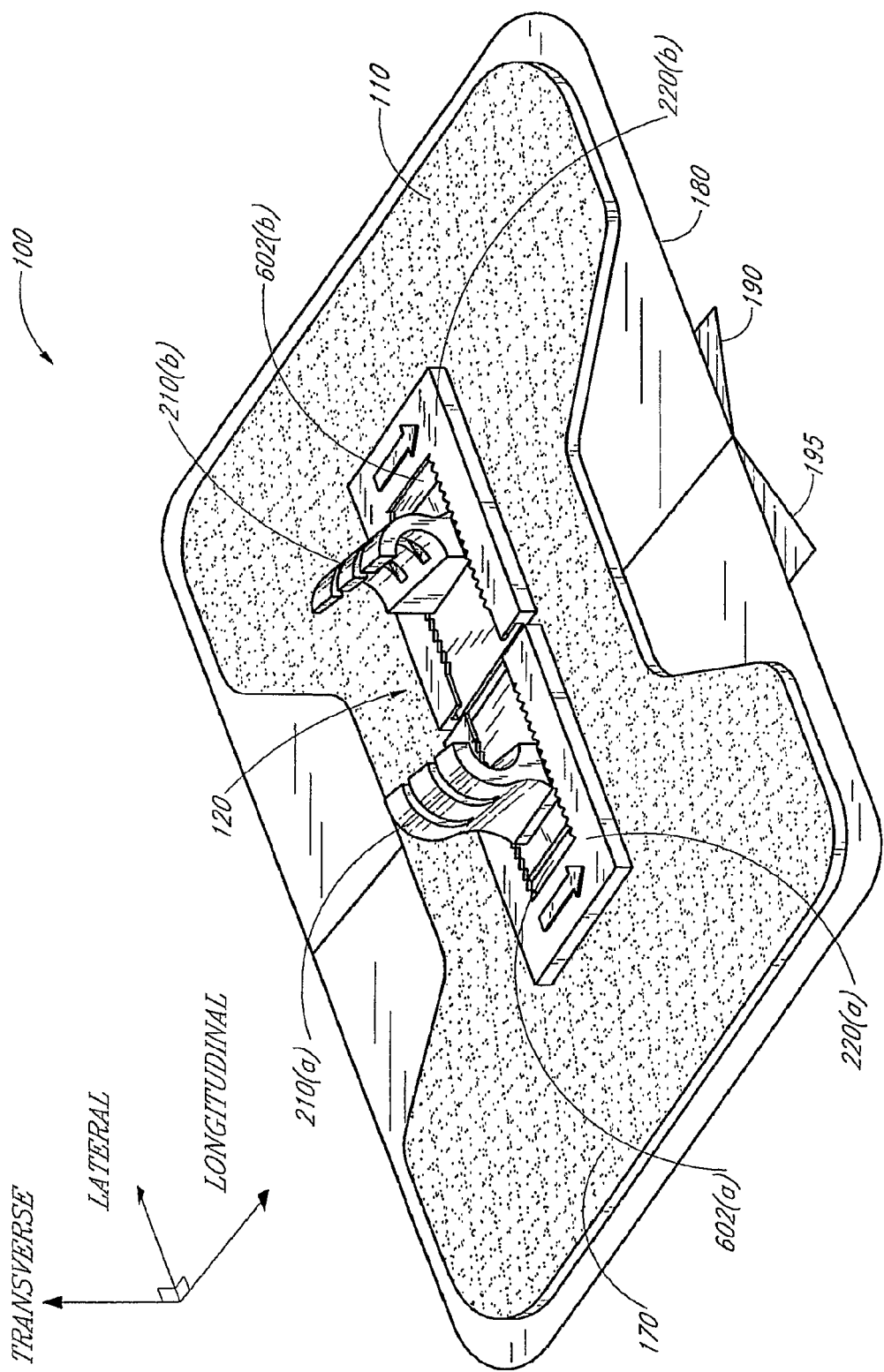
FIG. 12 is a perspective view of the securement device from FIG. 9 shown in an open position.

FIG. 12 is a perspective view of the retainer 120 from FIG. 9 shown in an open position. FIG. 13 is a front side view of the retainer 120 from FIG. 12 in a closed position. FIG. 14 is a cross-section view of the retainer 120 from FIG. 12.

As is illustrated in FIG. 9, the retainer 120 is configured to retain a portion of a medical article 400 having a tapering outer surface or shape. Thus, the central channel 140 preferably has a tapering inner surface and a radius that varies along the channel length. Additional embodiments of the central channel 140 of the retainer 120 can comprise a plurality of different radii and/or tapering regions. In this way, the size and shape of the central channel 140 can be chosen to match or to approximate the size and shape of the medical article 400 or portion thereof, e.g., the catheter hub, to be retained. By matching the inner surface contour of the central channel 140 to the outer surface of the secured portion of a medical article, a more effective securement may be achieved.

In addition or in the alternative, effective securement can also be achieved by the engagement of one or more abutment surface of the retainer 120 with one or more contact surfaces on the medical article 400. Additionally, the abutment surface can be used to arrest movement in one longitudinal direction and the shape of the channel 140 can be used to arrest movement in the opposite longitudinal direction. The tapering shape and abutment surface thus cooperate to inhibit longitudinal motion in both longitudinal directions.

At least a portion of the channel 140 can have a tapering inner surface and the retainer 120 can include an abutment surface in the form of a radically extending member of, or a proximal end of the retainer 120. For example, in the embodiment illustrated in FIGS. 9 through 14, the upper opening 150 has generally parallel sides while the channel 140 is tapered to match generally the shape of the medical article, thereby limiting longitudinal movement of the medical article 400 in the proximal direction. The retainer 120 includes slots 290 which cooperate with the push tab 310 of the medical article 400 to limit longitudinal movement of the medical article 400 in the distal direction. The upper opening 150 may include contouring (e.g., chamfers) along its periphery in order to guide the medical article 400 into the central channel 140 when inserting the medical article 400 into the retainer 120.

In such an embodiment, the tapering surface of the inner channel contacts an outer tapering surface of the medical article to limit motion in one longitudinal direction. Likewise, the proximal end of the retainer abuts with a radially extending member on the medical article to limit motion in the opposite longitudinal direction.

Although certain features of the retainer 120 can be specifically configured for use with a connector fitting, it will be understood by those of skill in the art that such a retainer 120 can be used with other adaptors or medical lines as well. Furthermore, the retainers described herein can be modified to more effectively cooperate with various types of connector fittings and adaptors.

Additional Embodiments

As understood from the above description of the embodiments of the securement device shown in FIGS. 1 through 8 and FIGS. 9 through 14, the securement device 100 arrests longitudinal movement of the retained section of the medical article 400 by interacting with at least one and preferably two contact surfaces of a radially extending member, which may constitute a radially extending member, tab, or other structure extending from the medical article 400. This approach for arresting longitudinal movement can also be used with other types of radially extending members or contacts (e.g., contact surfaces) on the medical article 400, the connector fitting or other medical articles or components thereof. For example, a retainer can be configured to capture or receive a tab, spline (e.g., a longitudinally extending spline) or collar on the connector fitting that is disposed on the distal side of the spin nut, or can capture all or a portion of the spin nut. In other embodiments, the retainer can be configured to fit between contacts on a medical article or medical articles. For example, the retainer 120 can be sized to fit between the spin nut 330 and the hexagonal collar 370(b) on the connector fitting 300 (see FIG. 26), between the hexagonal collars 370(a), 370(b), or between the proximal side of the spin nut 330 and the distal side of the catheter hub tab 310. In such cases, the end surfaces of the retainer 120 function as the abutment surfaces and cooperate with adjacent contacts on the medical article(s). Additionally, the retainer 120 can be configured to not only fit between two contacts on the medical article(s) but also can be configured to receive one or more radially extending members of the medical article(s).

Figure 15:
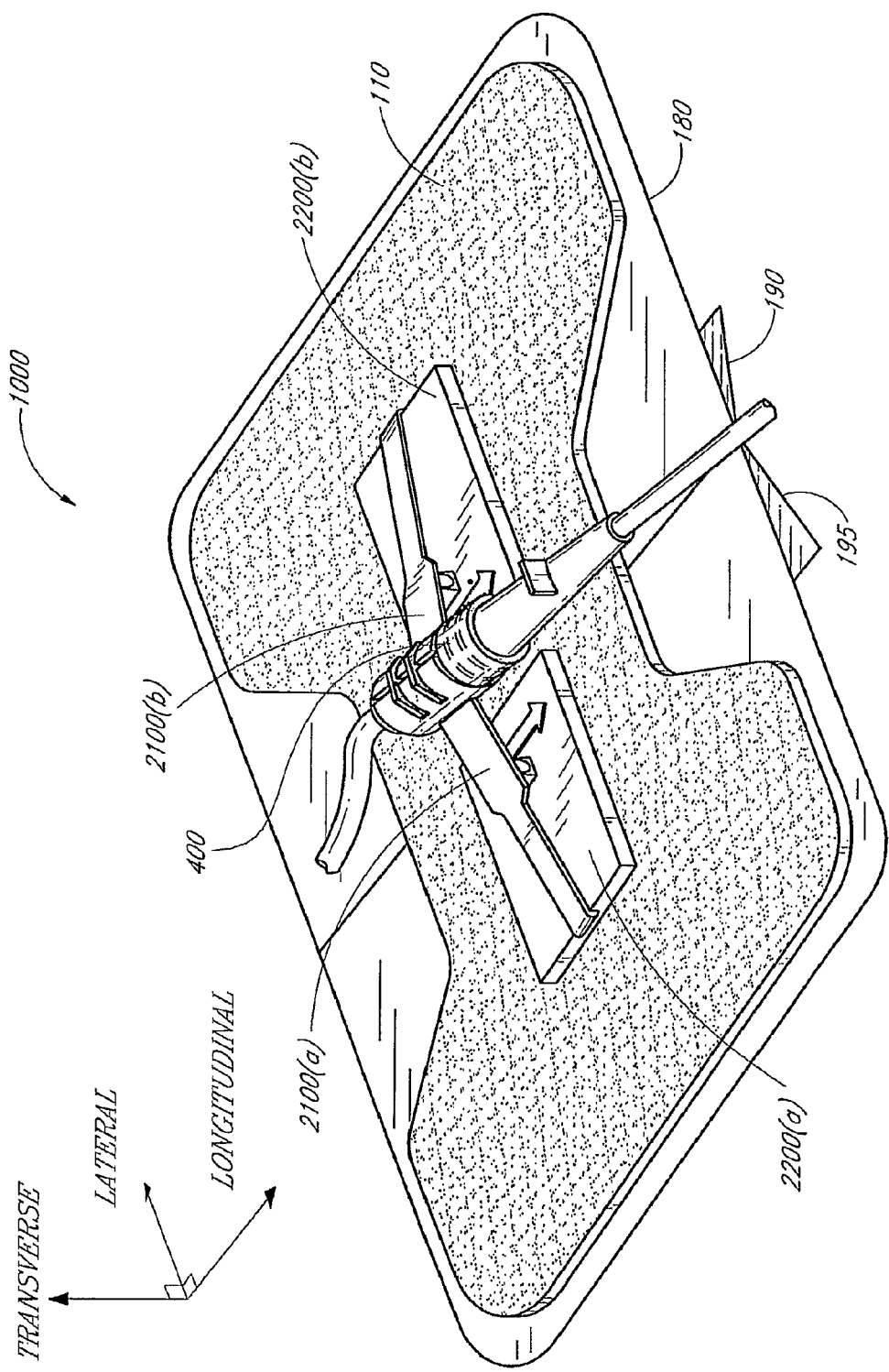
FIG. 15 is a perspective view of a securement device including a retainer having movable clips comprising lever arms, configured in accordance with a further preferred embodiment of the present invention and shown securing an exemplary medical article.
Figure 16:
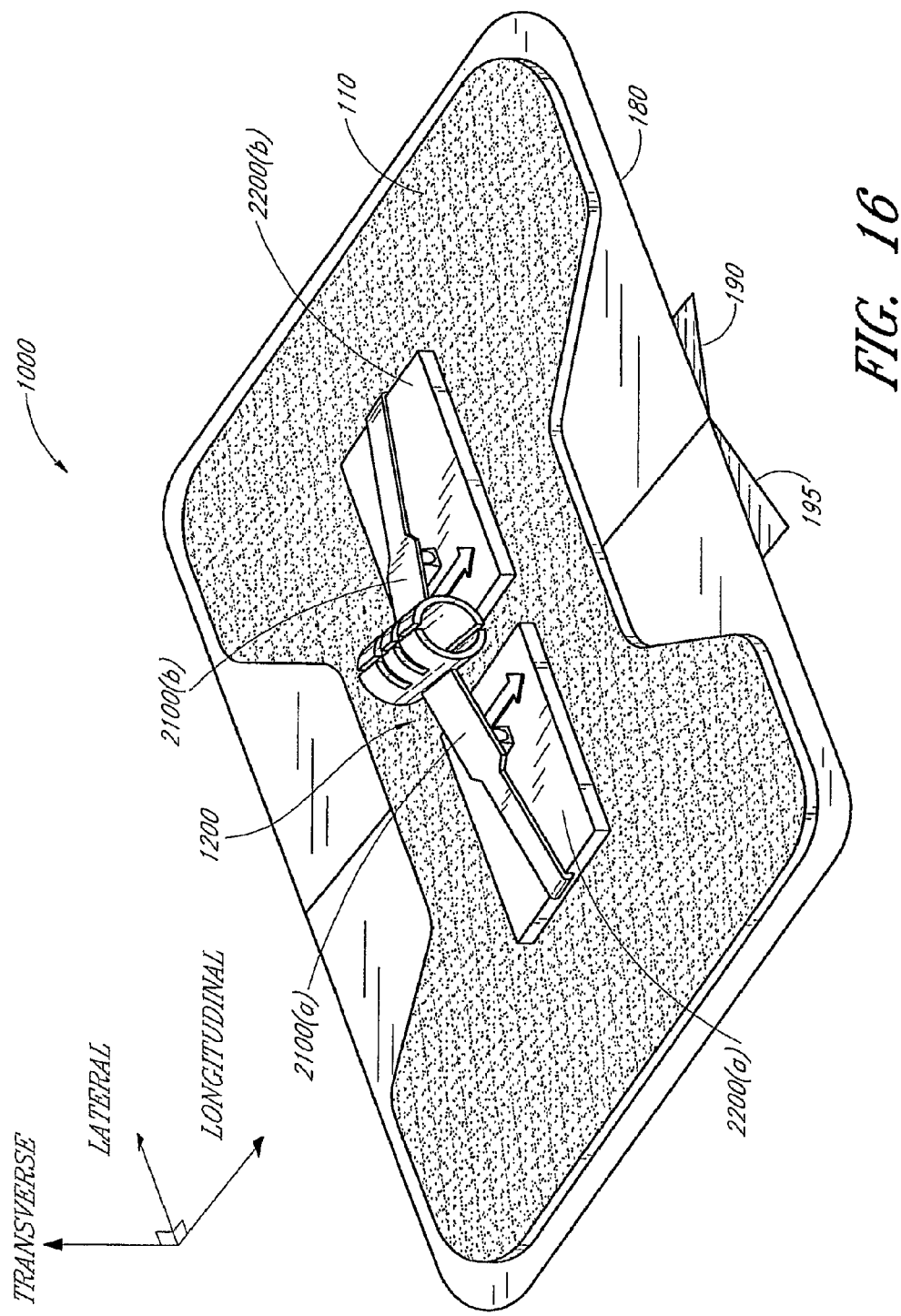
FIG. 16 is a perspective view of the securement device from FIG. 15 shown in a closed position.
Figure 17:
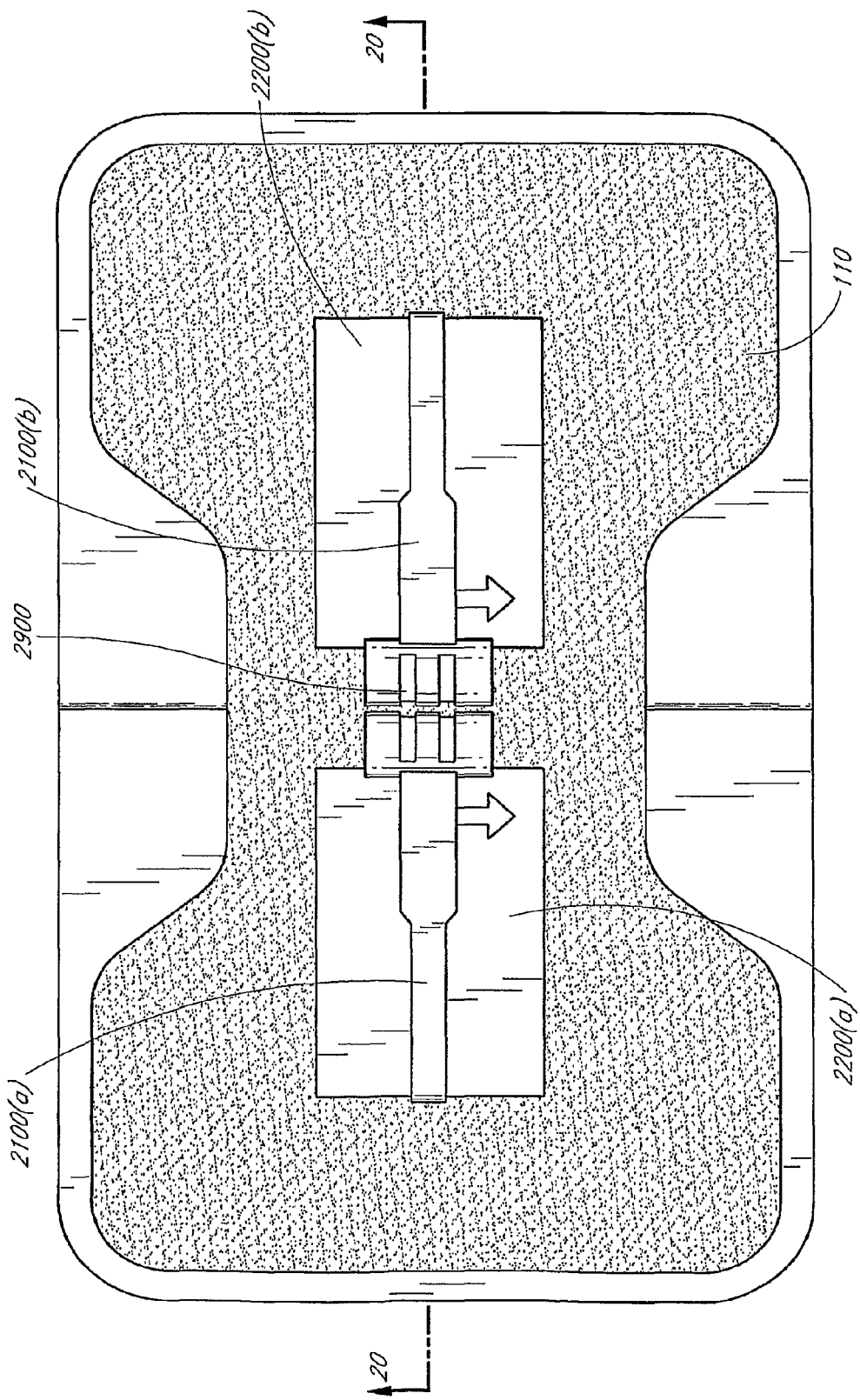
FIG. 17 is a top plan view of the securement device from FIG. 16 shown in a closed position.

Another preferred embodiment of such a design is described below in connection with FIGS. 15 through 20. FIG. 15 is a perspective view of a securement device 1000 including a retainer 1200 having clips 2100(a), 2100(b) and shown securing an exemplary medical article 400. FIG. 16 is a perspective view of the securement device 1000 shown in a closed position. FIG. 17 is a top plan view of the securement device 1000 shown in a closed position.

FIG. 18 is a front side view of the securement device 1000 with the retainer 1200 in an elevated, open position. As is illustrated in FIG. 18, this retainer design includes engagement members in the form of protrusions 295 which engage with engagement members in the form of receptacles 297 or contact points on the base 2200 to lock the retainer 1200 in the closed position. The features of this embodiment are similar to the features of the embodiment described with reference to FIGS. 1 through 8 except that the clips 2100(a), 2100(b) also move in a transverse direction (up and down) between a closed position and an open position. Though the illustrated embodiment employs lever arms to achieve this transverse motion, it will be appreciated that those of skill in the art will recognize that a variety of arrangements are possible as well.

FIG. 19 is a front side view of the securement device 1000 in a closed position. FIG. 20 is a cross section of the retainer 1200 taken along section 20-20 of FIG. 17. The closed position for the central channel 1400 of this embodiment is similar to the closed position for the embodiment illustrated in FIGS. 1 through 8 in that the central channel preferably has a generally constant cross-sectional shape (e.g., a generally constant diameter to cooperate with a tubular connector fitting body). Thus, longitudinal movement in the embodiment illustrated in FIGS. 15 through 20 is limited by the interaction of one or more abutment surfaces of the retainer 1200 (surfaces of the slots 2900, longitudinal ends, etc.) and contact surfaces of the medical article 400 (radially extending members, tabs, spin nuts, collars, etc.).

Alternatively, longitudinal movement can be fully arrested (i.e., arrested in both directions along the longitudinal axis) by (1) the interaction of an abutment on the retainer and a distally facing contact of the medical article in combination with (2) the shape of the channel 1400. An illustration of this approach is provided by the embodiment illustrated in FIGS. 21 through 24, which includes a retainer 1200 having a tapered inner channel 1400 and movable clips 2100(a), 2100(b) configured to at least move in a transverse direction (up and down) between a closed position and an open position. To inhibit longitudinal movement the medical article need not include a tab member 310 that fits within a slot 2900 and may instead have only a distal facing contact surface that abuts against the proximal end of the retainer 1200.

Figure 22:
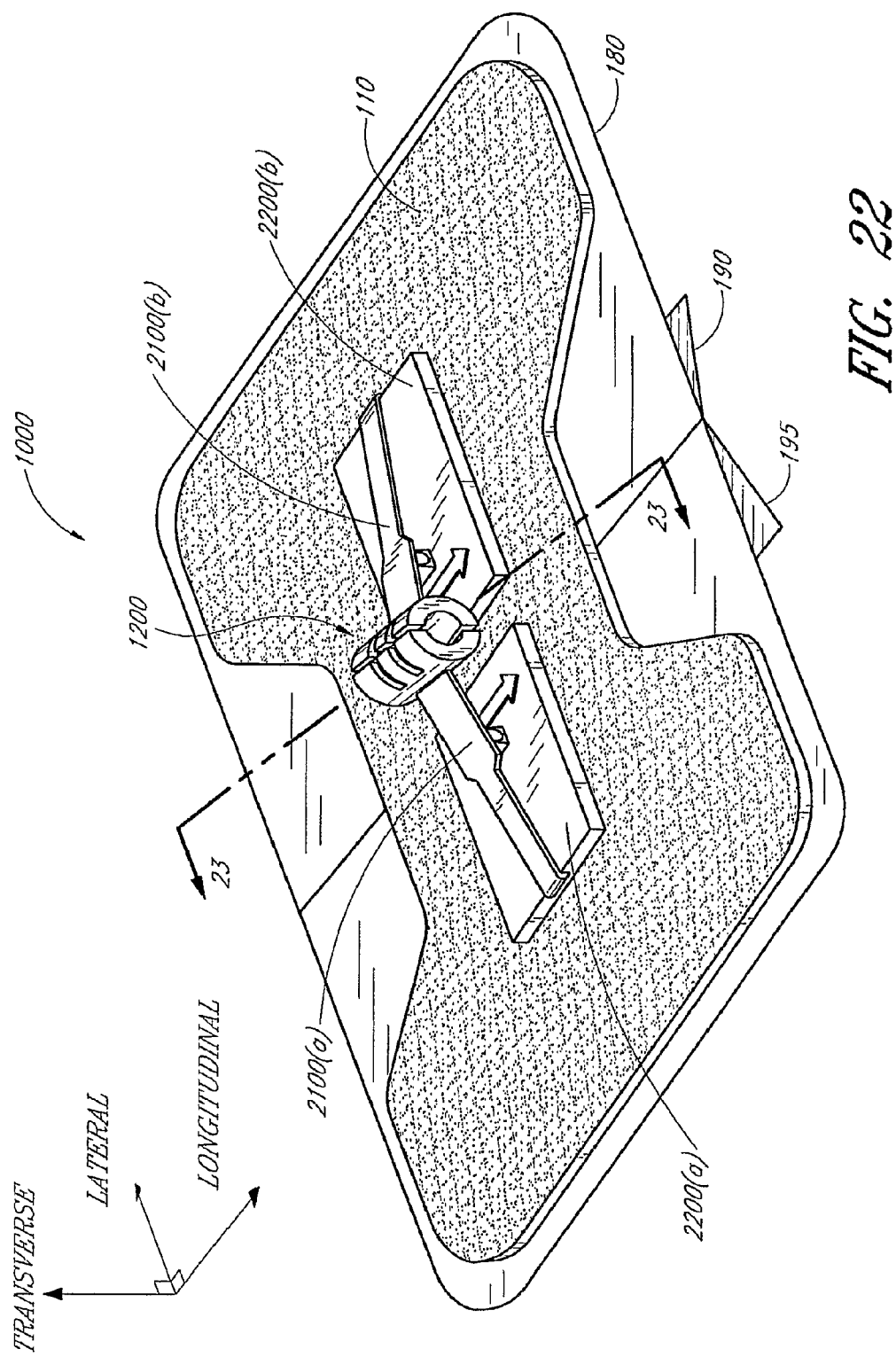
FIG. 22 is a perspective view of the securement device from FIG. 21 shown in a closed position.
Figure 23:
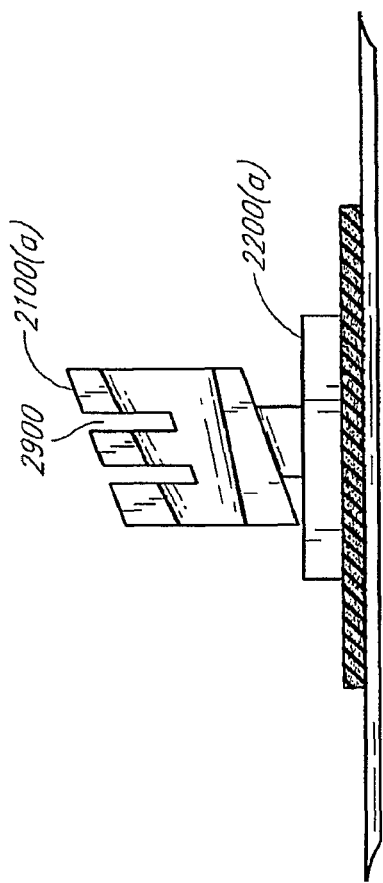
FIG. 23 is a cross-section view of the retainer taken along section 23-23 of FIG. 22.
Figure 24:
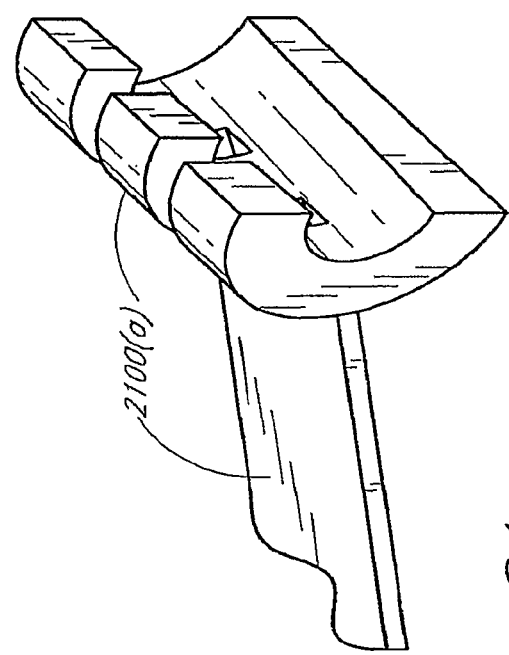
FIG. 24 is a perspective view of a left movable clip of the retainer from FIG. 22.

FIG. 21 is a perspective view of a securement device 1000 shown securing the exemplary medical article 400 and having a tapering inner channel 1400. FIG. 22 is a perspective view of the securement device 1000 shown in a closed position. FIG. 23 is a cross-section view of the retainer 1200. FIGS. 24A and 24B show perspective views of the left and right clips 2100(a) and 2100(b), respectively, of the retainer 1200.

In the illustrated embodiment, the tapering inner channel 1400 decreases in size in the proximal direction, thereby limiting longitudinal movement of the medical article 400 toward the insertion site. The interaction between a proximal-facing side wall of the slot 2900 and the distal side of the medical article tab 310 prevents longitudinal movement in the distal direction. Thus, some embodiments need only include one abutment where the channel has a tapering shape. Though the illustrated embodiment shows the medical article tab 310 interacting with a side wall of the slot 2900 to limit movement in the distal direction, such a restraint can also be achieved by other configurations as well. For example, the tab 310 can be configured to abut against the proximal face of the retainer 1200.

While not illustrated in the various embodiments, the channel can also have a tapering shape along at least a portion of its length and/or a step down in diameter along its length. The tapering shape can arrest longitudinal movement in one direction and an abutment, which is formed at the diameter step down, can interact with a corresponding contact (e.g., contact surface) on the medical article to arrest longitudinal movement in the opposite direction.

Additionally or in the alternative to the one or more abutment surfaces or tapering channels, at least a portion of the central channel in all of the illustrated embodiments can be at least partially coated with an adhesive (e.g., an adhesive that preferably releasably holds the fitting within the central channel) to limit or restrict longitudinal movement. Alternatively, the medical article can include an adhesive section to hold the medical article in the channel and/or relative to the retainer.

Medical Articles

An exemplary medical article 400 for use with the embodiments of the securement device described above will now be described with reference to FIGS. 25 and 26. The medical article 400 can be a single medical article or a combination of one or more medical articles. Such medical articles can be or include, for example, but without limitation, connector fittings, catheters, catheter hubs, catheter adaptors, fluid supply lines, or other similar articles.

Figure 25:
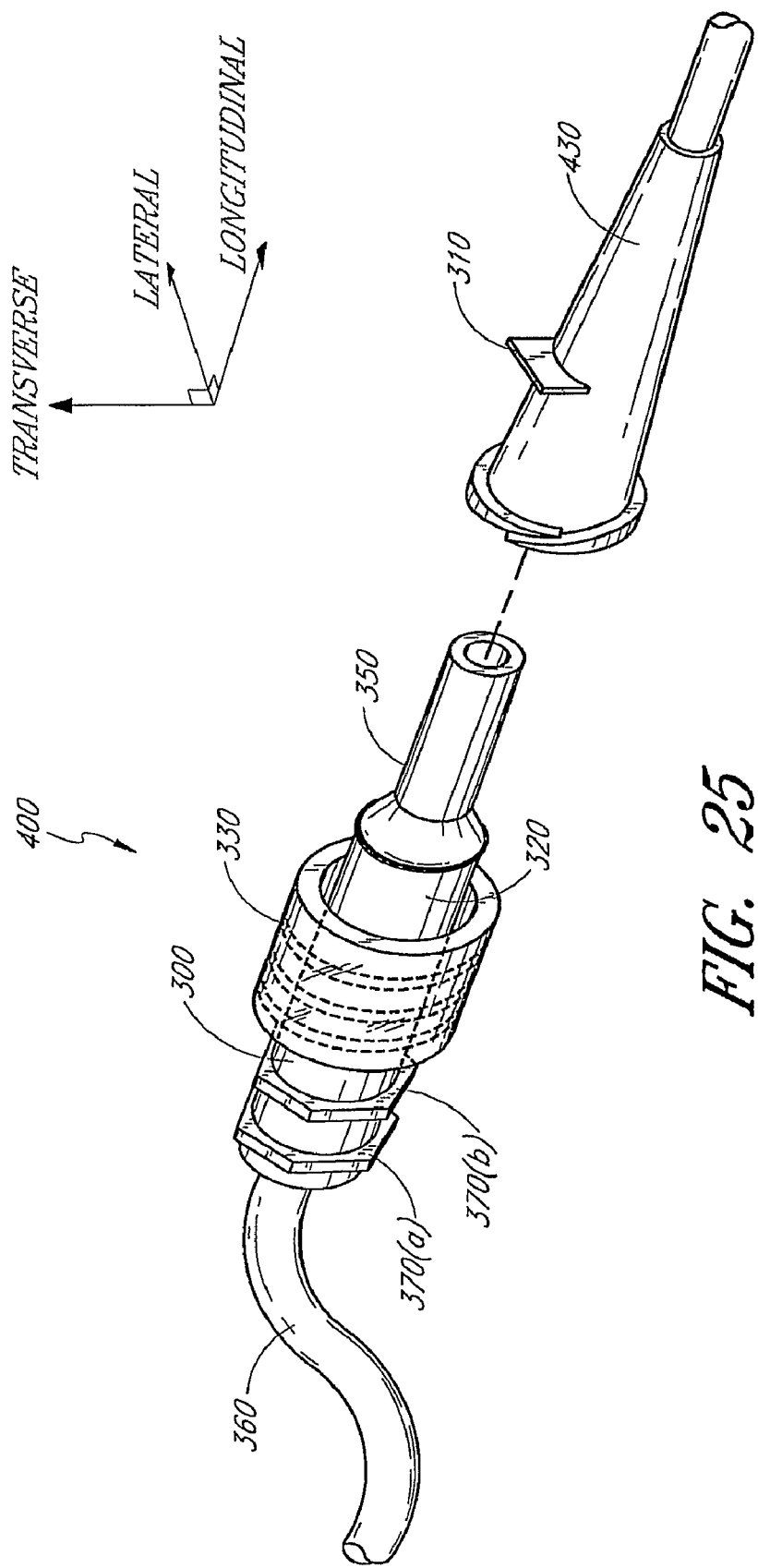
FIG. 25 is a perspective view of an exemplary connector fitting having a spin nut and a catheter hub with which the securement devices of FIGS. 1, 9, 15, and 21 can be used.

FIG. 25 is a perspective view of a catheter hub 430 and a connector fitting 300 with a spin nut 330. The connector fitting 300 is preferably disposed upon the end of a medical line 360 which can be connected to a drip bag, blood monitor, or other fluid related medical apparatus. While the retainer 120 of FIG. 3 is configured to receive a portion of the catheter hub 430, the retainer can be configured for use with the connector fitting 300, as will be described later.

The connector fitting 300 comprises an elongated body 320 which is attached to the end of the medical line 360. The connector fitting 300 also comprises a portion that is tapered along at least part of its longitudinal length so as to allow the end of this region to fit within the tapered conical portion of a catheter hub 430. The tapered portion 350 of the connector fitting 300 also preferably includes a centrally disposed lumen that communicates with the lumen of the medical line.

Figure 26:
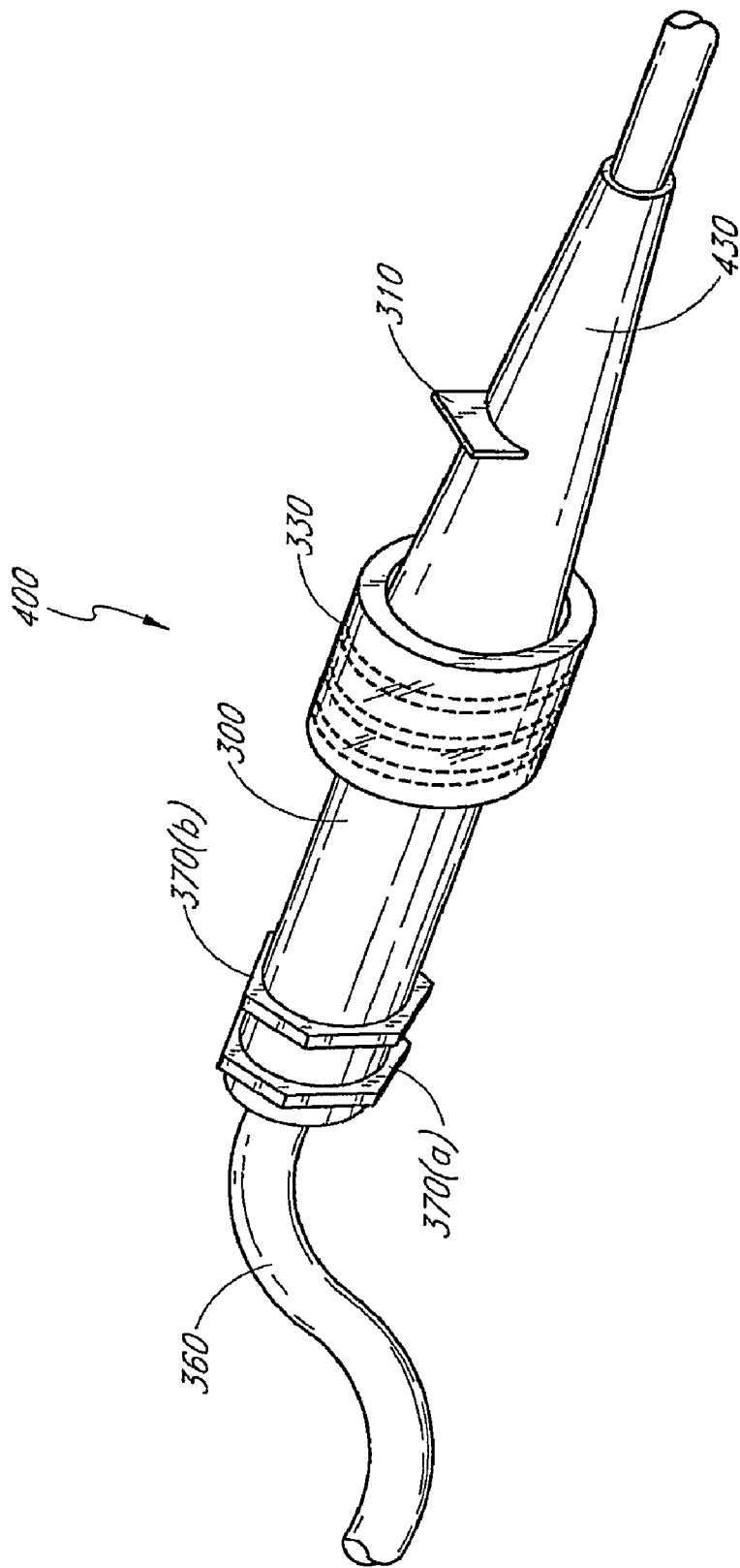
FIG. 26 is a perspective view of the connector fitting of FIG. 25 with the spin nut secured in the forward position and secured to the catheter hub.

FIG. 26 is a perspective view of the connector fitting 300 of FIG. 25 with the spin nut 330 secured in the proximal position and secured to the catheter hub 430. When the connector fitting 300 is inserted into the catheter hub 430, the lumen of the connector fitting is disposed in fluid communication with the lumen of the catheter hub 430. This provides fluid communication between the medical line 360 and the patient.

As seen in FIGS. 25 and 26, the connector fitting 300 has at least two contact surfaces in the form of one radially extending element 370(a) disposed upon an end of the elongated body 320 of the connector fitting 300 opposite the tapered end 350. It may be advantageous for the radially extending element 370(a) to extend completely around the circumference of the connector fitting 300. Additional contact surfaces in the form of a second radially extending element 370(b) can also be disposed upon the elongated body 320, as can additional radial elements (not shown). Those of skill in the art will recognize that the radially extending element or elements 370(a) need not have any particular shape or longitudinal thickness. Additionally, the radially extending elements need not have the same shape. For instance, the first radially extending element 370(a) can have the hexagonal shape illustrated and the second radially extending element 370(b) can have a circular shape.

A spin nut 330 is disposed upon the connector fitting 300 around the elongated body 320 of the fitting. The spin nut 330 is substantially cylindrical in form and is able to move upon the connector fitting 300. The spin nut 330 is capable of both rotational motion around the axis of the connector fitting and axial motion in both the proximal and distal directions along the length of the elongated body 320 of the fitting. The spin nut 330 also includes internal screw threads which are illustrated with phantom lines in FIGS. 25 and 26.

Still referring to FIGS. 25 and 26, a catheter hub 430 includes a body that, in the illustrated embodiment, is configured as a catheter hub and has a generally conical shape and tapers from a large radius to a smaller radius along its length.

In the illustrated embodiment, the catheter hub 430 comprises two contact surfaces that together form a radially extending member. The radially extending member can be, for example, a lateral tab 310 which is disposed at a position along the length of the body of the hub. The tab 310 can be gripped by the healthcare provider from the upper side of the retainer 120 in order to immobilize the catheter hub 430 when unscrewing the spin nut 330 or otherwise disengaging the connector fitting 300 from the catheter hub.

The catheter hub 430 also can include an external screw thread on the outside of the conical body near the end with the larger radius. The screw thread can be used in association with the spin nut 330 of the connector fitting 300 in order to securely interconnect the connector fitting 300 and the catheter hub 430.

The at least one retention surface 165 supports the medical article 400 so that the medical article 400 is elevated in the retainer 120, 1200 such that the retained portion of the medical article 400 (e.g., the retained portion of the catheter hub) is raised from the patient's skin to lessen or eliminate compression, excoriation, and/or chaffing of the skin. Thus, the retainer 120, 1200 lifts and holds the retained portion of the medical article from the patient's skin.

Operation

A preferred method of using the preferred embodiments of the securement device 100 will be described using the medical article 400 in the context of starting an intravenous line. However, the aspects and features of the operational method and the use of the present securement device are not limited to this particular application.

A healthcare provider preferably begins the procedure by inserting an IV catheter into patient's vein in a known manner and then attaching an intravenous line to the IV catheter though the luer connection. In particular, the healthcare provider inserts the tapered or luer end of the connector fitting into the catheter hub and then turns the spin nut to thread the spin nut over a thread flange disposed at the distal end of the catheter hub. This action draws together the two medical article components and releasably interlocks them. The immediate connection of the IV line to the catheter inhibits a back flow of blood through the catheter. The healthcare provider now preferably secures the IV catheter in place on the patient using the securement device 100, 1000. In some variations of this method, however, the securement device 100, 1000 can be first attached to one or both of the medical article (as well as the possibly to the patient) before the healthcare provider makes the connection between the two medical articles.

The healthcare provider moves the clips 210(a), 2100(a), 210(b), 2100(b) to the open position if the clips 210, 2100 were in a closed position. The healthcare provider then places the medical article 400 between the open clips and inline with the central channel of the retainer 120, 1200. The healthcare provider moves the clips to the closed position so as to capture the medical article within the central channel.

Depending on the diameter of the medical article 400, the inner surface of the channel can provide a close connection between the medical article 400 and the clips. The contact surfaces of the medical article 400 may form one or more radially extending members (e.g., one or more push tabs 310 or annular collars 370) or may form on the proximal or distal ends of the medical article. Preferably, the radially extending member(s) fits into one (or more) of the lateral slots 290 in the retainer. The tab 310 of the medical article lies within one of the slots 290, 2900 of the retainer 120, 1200. In addition, the body of the medical article 400 generally lies within the central channel of the retainer. When guided through the upper opening 150 by the healthcare provider when the clips 210(a), 2100(a), 210(b), 2100(b) are in the open position, the body of the medical article 400 will lie between the clips 210(a), 2100(a), 210(b), 2100(b) and between the sides of the central channel of the retainer 120, 1200. When the clips 210(a), 2100(a), 210(b), 2100(b) are moved to the closed position, the abutment surfaces (for example, of the sides of slot 290, 2900) will inhibit longitudinal migration of the medical article 400 through the central channel of the retainer 120, 1200.

In addition, if used with a connector fitting 300 in which a portion of the connector fitting, such as the spin nut 330, has a greater radial size than the size of the central channel 140 of the retainer 120, 1200, the spin nut 330 can act as a contact surface and will inhibit axial motion in one direction through the central channel of the retainer 120, 1200 as well. Using the size of the spin nut or other element having greater radial size than the size of the channel is not required for effective operation of the systems described herein; however, such a technique may be an effective form of securement or redundant securement in some applications.

The combination of the inner channel shape and the interengagement between the slot(s) 290, 2900 and the radially extending member(s) 310, 370, 330 on the medical article 400 arrest movement of the retained section of the medical line 400 in three dimensions: longitudinally, laterally and transversely once the retainer is placed in the closed position. Thus, the retainer 120, 1200 at least restricts, if not prevents, lateral and transverse movement of the retained section of the medical article. The additional features of the securement device 100 can restrict, if not prevent, longitudinal movement of the retained section of the medical article. The anchor pad 110 may or may not be attached to the patient before or after the medical article is secured within the retainer.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present retainer has been described in the context of particularly preferred embodiments, the skilled artisan will appreciate, in view of the present disclosure, that certain advantages, features and aspects of the retainer may be realized in a variety of other applications, many of which have been noted above. For example, while particularly useful for small-scale applications, such as the illustrated medical application, the skilled artisan can readily adopt the principles and advantages described herein to a variety of other applications, including larger scale devices.

Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims that follow.

What is claimed is:

1. A securement system, comprising:
   a retainer comprising a first clip and a second clip, the first and second clips being slidable in at least a lateral direction with respect to one another to establish a closed condition and an open condition, the first and second clips cooperating to form a channel between the first clip and the second clip, when the retainer is in the closed condition, the first clip having at least one surface which extends in a direction normal to the axis of the channel of the retainer;
   an anchor supporting the retainer so that the first and second clips are inhibited from moving generally in the direction normal to the axis of the channel; and
   a medical article comprising an elongated body and at least one radially extending member that extends from the elongated body in a direction normal to the axis of the elongated body, wherein the radially extending member of the medical article abuts the at least one surface of the retainer when the retainer is in the closed condition to inhibit longitudinal motion of the medical article through the retainer.

2. A securement system as in claim 1, wherein the radius of the channel tapers along the longitudinal length of the channel.

3. A securement system as in claim 1, wherein the radius of the channel is constant along its longitudinal length.

4. A securement system as in claim 1 wherein the channel of the retainer is formed between a first groove disposed upon the first clip and a second groove disposed upon the second clip such that the first groove and the second groove cooperate when the retainer is in the closed condition to form the channel of the retainer.

5. A securement system as in claim 1 further comprising a first base and a second base, each base being attached to the anchor and having a ratchet element, each of the first and second clips being slidingly mounted in one of the ratchet elements so as to move between the closed condition and the open condition.

6. A securement system as in claim 5, wherein at least one of the first and second bases and one of the ratchet elements are a unitary structure.

7. A securement system as in claim 5, wherein the first base and the second base are a unitary structure.

8. A securement system as in claim 1, wherein the channel additionally comprises at least one annular slot disposed along the length of the channel.

9. A securement system as in claim 8, wherein the at least one surface of the body is a lateral face of the at least one annular slot.

10. A securement system as in claim 9, wherein the radially extending member of the medical article is positioned within the slot of the channel when the radially extending member abuts the at least one surface of the retainer.

11. A securement device for securing a medical article having an elongated body to a body of a patient, comprising:
    a flexible anchor having a mounting surface at least partially covered by an adhesive layer for attaching the securement device to the patient's body; and a retainer attached to an upper side of the anchor and having a first clip and a second clip, the first clip having a first groove and the second clip having a second groove, at least one of the first and second clips being slidable in at least a lateral direction so as to define a channel between the first and second clips when in a closed position, the channel being formed by the first and second grooves.

12. A securement device as in claim 11, wherein at least a portion of the surface of the channel extends about a central axis of the channel by more than 180 degrees.

13. A securement device as in claim 11, wherein the channel has a tapering surface.

14. A securement system, comprising:
a retainer comprising a body having a first portion and a second portion, the first and second portions being slidable in a lateral direction with respect to one another to establish a closed condition and an open condition, the first and second portions cooperating to form a channel between the first and second portions when the retainer is in the closed condition, the first portion of the body having at least one surface which extends in a direction normal to the axis of the channel of the retainer; and
a medical article comprising an elongated body and at least one radially extending member that extends from the elongated body in a direction normal to the axis of the elongated body, wherein the radially extending member of the medical article abuts the at least one surface of the retainer when the retainer is in the closed condition to inhibit longitudinal motion of the medical article through the retainer.

15. A securement system as in claim 14, wherein the radius of the channel tapers along the longitudinal length of the channel.

16. A securement system as in claim 14, wherein the channel additionally comprises at least one annular slot disposed along the length of the channel.

17. A securement system as in claim 14, wherein the retainer comprises a latch mechanism disposed between the body and the first and second portions.

18. A securement system as in claim 14, wherein the first and second portions each define a groove.

19. A securement system as in claim 14, wherein at least one of the first and second portions comprises a protrusion, and wherein the body comprises a receptacle configured to receive the protrusion to establish the closed condition.

20. A securement system as in claim 19, wherein a direction of movement of each of the first and second portions includes transverse and lateral components.

21. A securement system as in claim 18, wherein the grooves cooperate together when the retainer is in the closed position to form the channel of the retainer.

22. A method of releasably securing a medical article to a retainer, the method comprising the steps of:
providing a medical article comprising an elongated body and at least one radially extending member that extends from the elongated body in a direction normal to the axis of the elongated body;
providing a retainer comprising a first clip, a first base, a second clip, and a second base, the first clip slidingly engaging the first base and the second clip slidingly engaging the second base, the first and second clips having a closed configuration in which the first and second clips are slid toward each other and relative to the first and second bases, the first and second clips having an open configuration in which the first and second clips are slid away from each other and relative to the first and second bases, the retainer further comprising a first groove disposed upon the first clip and a second groove disposed upon the second clip such that when the retainer is in the closed position the first groove and the second groove cooperate to form a channel, and at least one slot disposed along the length of the channel;
sliding the first and second clips in opposite directions along an axis to place the retainer in the open configuration;
placing the elongated body of the medical article between the first and second grooves of the retainer;
coarsely aligning the radially extending member with the at least one slot; and
attaching the medical article to the retainer by sliding the first and second clips in opposite directions along the axis to place the retainer in the closed configuration and capture the radially extending member in the at least one slot.

* * * * *